(12) United States Patent
Yoneyama

(10) Patent No.: US 7,175,598 B2
(45) Date of Patent: Feb. 13, 2007

(54) ULTRASOUND DIAGNOSIS APPARATUS THAT ADJUSTS A TIME PHASE BETWEEN A PLURALITY OF IMAGE SERIES

(75) Inventor: Naoki Yoneyama, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 249 days.

(21) Appl. No.: 10/463,614

(22) Filed: Jun. 18, 2003

(65) Prior Publication Data

US 2004/0044283 A1    Mar. 4, 2004

(30) Foreign Application Priority Data

Jun. 18, 2002    (JP) ............................. 2002-176893

(51) Int. Cl.
*A61B 8/00*      (2006.01)
(52) U.S. Cl. ..................................... 600/443
(58) Field of Classification Search ................ 600/441, 600/443–447, 454–456, 458, 483, 513; 128/916
See application file for complete search history.

(56) References Cited

U.S. PATENT DOCUMENTS

| | | | | |
|---|---|---|---|---|
| 5,435,310 A | * | 7/1995 | Sheehan et al. ............. | 600/416 |
| 5,481,279 A | * | 1/1996 | Honda et al. ................ | 345/533 |
| 5,997,883 A | * | 12/1999 | Epstein et al. .............. | 324/306 |
| 6,447,450 B1 | * | 9/2002 | Olstad ........................ | 600/437 |
| 6,447,453 B1 | * | 9/2002 | Roundhill et al. .......... | 600/443 |
| 6,514,207 B2 | * | 2/2003 | Ebadollahi et al. ......... | 600/450 |
| 6,558,325 B1 | * | 5/2003 | Pang et al. .................. | 600/443 |
| 6,673,017 B1 | * | 1/2004 | Jackson ...................... | 600/437 |
| 6,730,032 B2 | * | 5/2004 | Yamauchi .................... | 600/443 |

FOREIGN PATENT DOCUMENTS

JP          10-99328         4/1998

* cited by examiner

*Primary Examiner*—Francis J. Jaworski
(74) *Attorney, Agent, or Firm*—Oblon, Spivak, McClelland, Maier & Neustadt, P.C.

(57) ABSTRACT

An ultrasound diagnosis apparatus comprises an insonifier, a receiver, and a processor. The insonifier is configured to insonify an ultrasound to a specimen. The receiver is configured to receive an echo signal from the specimen resulting from the ultrasound. The processor is in communication with the receiver. Further, the processor is configured to process the echo signal so as to obtain a first series of images under a first condition and a second series of images under a second condition. The processor is also configured to measure a first physical value on the first series of images and a second physical value on the second series of images. The processor is further configured to adjust a time phase of the second series of images relative to a time phase of the first series of images based on the first physical value and the second physical value.

32 Claims, 16 Drawing Sheets

FOUR-CHAMBER VIEW IMAGES: | 410 | 420 | 430 | 440 | 450 | 460 | 470 | 480 | 490 |

TWO-CHAMBER VIEW IMAGES: | 210 | 220 | 230 | 240 | 250 |   | 260 |   | 270 |

1st CROSS-SECTIONAL VIEW: 410, 420, 430, 440, 450, 460, 470, 480, 490

2nd CROSS-SECTIONAL VIEW: 210, 220, 230, 240, 250, 260, 270

3rd CROSS-SECTIONAL VIEW: 310, 320, 330, 340, 350, 360, 370

ULTRASOUND DIAGNOSIS APPARATUS THAT ADJUSTS A TIME PHASE BETWEEN A PLURALITY OF IMAGE SERIES

CROSS-REFERENCE TO RELATED APPLICATION

This application is based upon and claims the benefit of priority from prior Japanese Patent Application No. P2002-176893, filed on Jun. 18, 2002, the entire contents of which are incorporated herein by reference.

FIELD OF THE INVENTION

The present invention relates to an ultrasound diagnosis apparatus which acquires a plurality of image series under respective different conditions. The ultrasound diagnosis apparatus is operative to adjust a time phase between the plurality of image series. The present invention further relates to a method of adjusting the time phase between the plurality of image series acquired in a medical equipment.

BACKGROUND OF THE INVENTION

An ultrasound diagnosis apparatus insonifies ultrasound pulses to a patient or an object (hereinafter referred to as a specimen). The ultrasound pulses are generated from transducers built in an ultrasound probe. The ultrasound diagnosis apparatus then receives echo signals from the specimen with the ultrasound transducers. The echo signals occur due to a difference of acoustic impedances among tissues of the specimen.

Such a diagnosis technique mentioned above requires easy operations, such as contacting the ultrasound probe with a surface of a body of the specimen. The operations are usually performed by a doctor or the like (hereinafter referred to as an operator). Therefore, the operator can easily observe two-dimensional ultrasound images in real time. The diagnosis technique is widely used for functional and/or morphological diagnoses of organs, such as a heart. Particularly, in an ultrasound diagnosis for an area around the heart, it is very important to evaluate heart functions objectively and quantitatively. Therefore, items to be measured in the diagnosis for the heart usually include a kinetic rate of heart tissues, a speed of blood stream, and an area and/or a volume of heart chambers.

When a motor function of the heart is diagnosed, images are displayed as a moving image and it is preferably desired to make the diagnosis on the basis of three-dimensional information. In order to meet such a clinical desire or requirement, it is expected to put a real-time three-dimensional scan technique into a practical use in the future. Currently, however, it does this with a plurality of two-dimensional moving images acquired from respective different directions against the heart. Images included in the respective moving images obtained in the above manner are tried to be displayed in a time phase adjusted manner in a single display. The time phase can be defined as time of image acquisition in repeated cycles of heartbeats. One example requiring a time phase adjustment may be a simultaneous display of tomograms along a major axis of the heart and tomograms along a minor axis of the heart. Another example may be a simultaneous display of a moving image of a predetermined part of the heart under a normal condition and a moving image of the predetermined part immediately after an exercise stress has been given to the specimen. The other example mentioned above may be called an exercise stress echocardiography.

Further, there is a technique of measuring a volume of a heart chamber based on two tomograms, which are orthogonal with each other. For example, four-chamber view image data and two-chamber-view image data are acquired in a form of a moving image, respectively. In this case, the volume of heart chambers is measured on the basis of the image data according to the measurement technique. The four-chamber view image may represent a tomogram showing two atrials and two ventricles of the heart. The two-chamber view image may represent a tomogram showing one atrial and one ventricle of the heart.

In an ultrasound diagnosis technique with an intent to examine such heart functions, it is important to adjust a time phase of cardiac pulsation (heart strokes) between two moving images. This is particularly important in the event of displaying two moving images each of which are under a different imaging condition or in the event of calculating a volume based on such two moving images. Hereinafter, sequential image data (time-series image data) acquired as a moving image or picture are referred to as sequential images or sequential image data.

In the above ultrasound diagnosis technique, it generally utilizes a heartbeat synchronous technique wherein, for example, electrocardiographic complex information is acquired during the acquisition of the ultrasound images. Alternatively, for example, the ultrasound images are sequentially acquired in synchronization with R-waves of an electrocardiographic complex. According to the former case, ultrasound image data are acquired with an electrocardiographic complex under each of different conditions (e.g., a four-chamber view image acquisition and a two-chamber view image acquisition). When these image data are reproduced and displayed, image data obtained under the four-chamber view image acquisition and image data obtained under the two-chamber view image acquisition are sequentially displayed, for example, side by side in a single display. Each of those image data is for an image acquired in every predetermined time period after the R-wave has occurred. Further, various measurements including a volume calculation of the heart chamber are made based on these image data. In this regard, when an image in a predetermined time phase is selected, it is also quite common to set an image number (or a frame number) of the ultrasound images so as to determine the selected image, instead of setting a time period elapsed from the R-wave occurrence. The frame number is determined on the basis of time instant of the R-wave occurrence.

As described above, application of a heartbeat synchronous technique to two different kinds of sequential images enables the display of two heart images in time phase, each of which under a different condition. This has resulted in a great improvement in measurements of the heart function by ultrasound pulses.

When, however, a time phase of the ultrasound images is determined (or set) based on the electrocardiographic complex in a conventional manner, intervals between R-waves of an electrocardiographic complex may not always be constant. Particularly, specimens to undergo cardiac examinations are likely to suffer from an arrhythmia. Further, even if it is a normal healthy person, it is obvious that intervals between R-waves of the electrocardiographic complex are outstandingly short after the exercise stress has been given to the person. Still further, it is known that intervals between R-waves of the electrocardiographic complex are not regularly short and long in some cases of a heart disease, but rather, for example, different in proportions between a systolic period and a diastolic period.

Drawbacks of the conventional technique will be described in FIG. 1 in an exemplary case that a diastolic period of the electrocardiographic complex varies temporally regarding a predetermined specimen. FIG. 1 is an illustration showing a relationship of sequential images between two predetermined R-wave intervals of an electrocardiographic complex according to a prior art of the present invention. In FIG. 1, FIG. 1(a) shows the electrocardiographic complex. FIG. 1(b) shows image numbers of sequential images in two different predetermined time periods (or frame numbers of ultrasound images in the two predetermined R-wave intervals). FIG. 1(c) shows volumes of a heart chamber in the sequential images. For example, N0+1 images of a four-chamber view (a first image series) are sequentially acquired during an interval between an R-wave R1 and an R-wave R2 (hereinafter referred to as an interval R1–R2) of the electrocardiographic complex. Also, N0 images of a two-chamber view (a second image series) are sequentially acquired during an interval between an R-wave R3 and an R-wave R4 (hereinafter referred to as an interval R3–R4) of the electrocardiographic complex. In the interval R1–R2, a first image (image 1) may be acquired in a time t1 after the R-wave R1 occurrence. A second image (image 2) may be acquired in a time t2 after the R-wave R1 occurrence. Similarly, an N0th image (image N0) may be acquired in a time tN0 after the R-wave R1 occurrence. In FIG. 1(c), a period from a peak to a valley in each of the intervals R1–R2 and R3–R4 may be called a systolic period. Further, a period from a valley to a peak in each of the intervals R1–R2 and R3–R4 may be called a diastolic period. A time of the peak may be called an end-diastolic time. A time of the valley may be called an end-systolic time.

When it comes to an exercise stress echocardiography, images of the specimen before an exercise may be acquired, for example, during the interval R1–R2. Similarly, images of the specimen after the exercise may be acquired, for example, during the interval R3–R4.

Usually an image acquisition time is almost constant for any one of ultrasound images. Therefore, when a diastolic period in the interval R3–R4 is shorter than a diastolic period in the interval R1–R2, an end-diastolic time Q1 in the interval R1–R2 may correspond to an (N0+1)th image (or frame) of the first image series while an end-diastolic time Q2 in the interval R3–R4 corresponds to an N0th image (or frame) of the second image series. As described in the above example, when a diastolic period and/or a systolic period temporally varies, it is difficult to properly comprehend a time phase or a relationship between the first image series and the second image series if such a time phase is interpreted in accordance with an image obtained in a predetermined time after a respective R-wave occurrences in an electrocardiographic complex. It is also difficult if such a time phase is interpreted in accordance with an image number (or a frame number) of images included in a respective predetermined R-wave interval. Therefore, it causes difficulties in a time phase adjusted display and/or various kinds of measurements in time phase based on the first image series and the second image series.

BRIEF SUMMARY OF THE INVENTION

According to a first aspect of the present invention, there is provided an ultrasound diagnosis apparatus which comprises an insonifier, a receiver, and a processor. The insonifier is configured to insonify an ultrasound to a specimen. The receiver is configured to receive an echo signal from the specimen resulting from the ultrasound. The processor is in communication with the receiver. Further, the processor is configured to process the echo signal so as to obtain a first series of images under a first condition and a second series of images under a second condition. The processor is also configured to measure a first physical value on the first series of images and a second physical value on the second series of images. The processor is further configured to adjust a time phase of the second series of images relative to a time phase of the first series of images based on the first physical value and the second physical value.

According to a second aspect of the present invention, there is provided an ultrasound diagnosis apparatus which comprises an insonifier, a receiver, and a processor. The insonifier is configured to insonify an ultrasound to a specimen. The receiver is configured to receive an echo signal from the specimen resulting from the ultrasound. The processor is in communication with the receiver. Further, the processor is configured to process the echo signal so as to obtain a first series of images when insonified under a first condition and a second series of images when insonified under a second condition. The processor is also configured to detect a first, a second, and a third characteristic times in a first predetermined period when the first series of images have been obtained and a fourth, a fifth, and a sixth characteristic times in a second predetermined period when the second series of images have been obtained. The processor is further configured to adjust a time phase of the first series of images and a time phase of the second series of images based on the first to the sixth characteristic times.

According to a third aspect of the present invention, there is provided a medical image apparatus which comprises a generator and a processor. The generator is configured to generate a first series of medical images under a first condition and a second series of medical images under a second condition. The processor is in communication with the generator. Further, the processor is configured to measure a first physical value on the first series of medical images and a second physical value on the second series of medical images, and to adjust a time phase of the second series of medical images relative to a time phase of the first series of medical images based on the first physical value and the second physical value.

According to a fourth aspect of the present invention, there is provided a data processor which receives a series of medical data obtained in a medical equipment. The processor comprises an interface and a processor. The interface is configured to receive a first of the series of medical data obtained under a first condition in the medical equipment and a second of the series of medical data obtained under a second condition in the medical equipment. The processor is configured to measure a first physical value on the first series of medical data and a second physical value on the second series of medical data, and to adjust a time phase of the second series of medical data relative to a time phase of the first series of medical data based on the first physical value and the second physical value.

According to a fifth aspect of the present invention, there is provided a method of adjusting a time phase of a second series of medical data obtained under a second condition in a medical equipment relative to a time phase of a first series of medical data obtained under a first condition in the medical equipment. The method comprises steps of measuring a first physical value on the first series of medical data, measuring a second physical value on the second series of medical data, and adjusting the time phase of the second series of medical data relative to the time phase of the first series of medical data based on the first physical value and the second physical value.

According to a sixth aspect of the present invention, there is provided a computer program product on which is stored a computer program for adjusting a time phase of a second series of medical data obtained under a second condition in a medical equipment relative to a time phase of a first series of medical data obtained under a first condition in the medical equipment. The computer program has instructions, which when executed, perform steps comprising measuring a first physical value on the first series of medical data, measuring a second physical value on the second series of medical data, and adjusting the time phase of the second series of medical data relative to the time phase of the first series of medical data based on the first physical value and the second physical value.

According to a seventh aspect of the present invention, there is provided a medical image apparatus which comprises a generator and a processor. The generator is configured to generate a first series of medical images during a first period and a second series of medical images during a second period different from the first period. The processor is in communication with the generator. Further, the processor is configured to measure a first physical value on the first series of medical images and a second physical value on the second series of medical images and to adjust a time phase of the second series of medical images relative to a time phase of the first series of medical images based on the first physical value and the second physical value.

According to an eighth aspect of the present invention, there is provided a medical diagnostic apparatus that adjusts a time phase between a plurality of image series. The apparatus comprises a transmitter, a receiver, a processor, and a memory storage device. The transmitter is configured to provide a first signal to a specimen. The receiver is configured to receive a second signal from the specimen that is related to the first signal. The processor is in communication with the receiver that receives the second signal from the receiver. The memory storage device is coupled to the processor. Further, the memory storage device stores the image series. The processor is also operative to generate a plurality of data sets from the second signal and store each of the data sets as the image series within the memory storage device. The processor is further operative to determine a profile from each of the image series. The processor is still further operative to adjust the profile of a first of the image series relative to the profile of a second of the image series based upon a comparison of a physical value determined from each of the first of the image series and the second of the image series.

BRIEF DESCRIPTION OF THE DRAWINGS

A more complete appreciation of embodiments of the present invention and many of its attendant advantages will be readily obtained by reference to the following detailed description considered in connection with the accompanying drawings, in which:

FIG. 15 is an illustration showing another example of thumbnails, displayed in parallel, of the time-phase adjusted three kinds of sequential images according to the second embodiment of the present invention;

DETAILED DESCRIPTION OF THE PREFERRED EMBODIMENTS

Embodiments of the present invention will be described with reference to the accompanying drawings.

(First Embodiment)

An ultrasound diagnosis apparatus according to a first embodiment of the present invention will be described with reference to FIGS. 2 to 10. In the first embodiment of the present invention, a volume of an inner space of a heart chamber is measured for each image included in two (kinds of) sequential image data (or two different series of images). The two sequential image data are obtained for a same specimen under two different conditions, respectively. The two sequential image data may comprise first sequential image data and second sequential image data. The first sequential image data may represent various time-series aspects of a four-chamber view of the heart. The second sequential image data may represent various time-series aspects of a two-chamber view of the heart. The four-chamber view is a view of the heart orthogonal with the two-chamber view. The view results from ultrasound scanning. After the volume measurements, a first systolic period and a first diastolic period of the heart are determined, respectively, in accordance with a temporal response of the volumes measured on the four-chamber view in the images included in the first sequential image data. Similarly, a second systolic period and a second diastolic period of the heart are determined, respectively, in accordance with a temporal response of the volumes measured on the two-chamber view in the images included in the second sequential image data. Accordingly, a time phase of the second sequential image data may be adjusted to a time phase of the first sequential image data based on the number of images obtained in a period corresponding to each of the first systolic period, the first diastolic period, the second systolic period, and the second diastolic period. Further, after the time phase adjustment, a volume of the internal space of the heart chamber may be measured, using third sequential image data calculated based on the time phase adjusted first sequential image data and second sequential image data.

Figure 1:
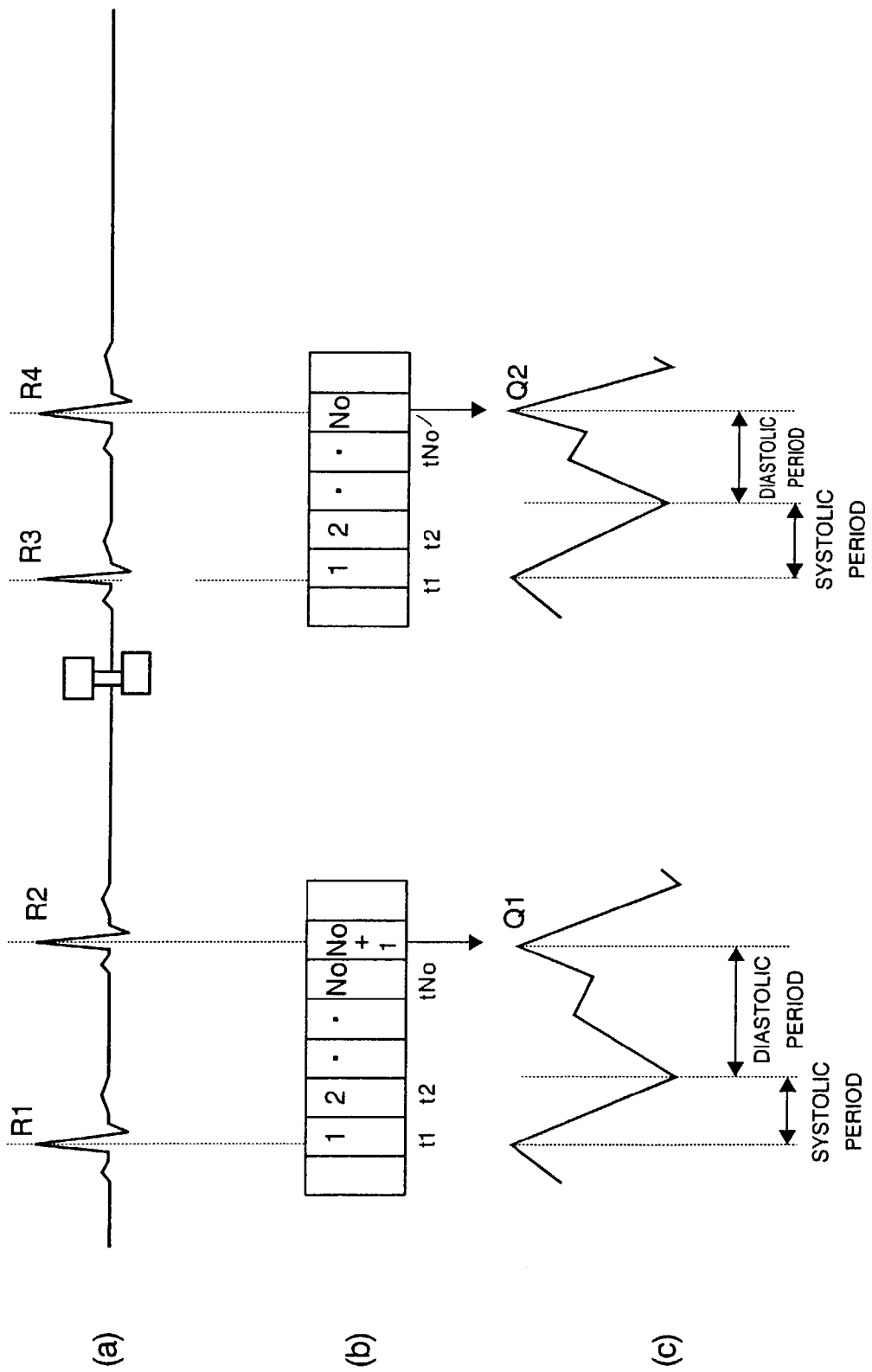
FIG. 1 is an illustration showing a relationship of sequential images between two predetermined R-wave intervals of an electrocardiographic complex according to a prior art of the present invention.
Figure 2:
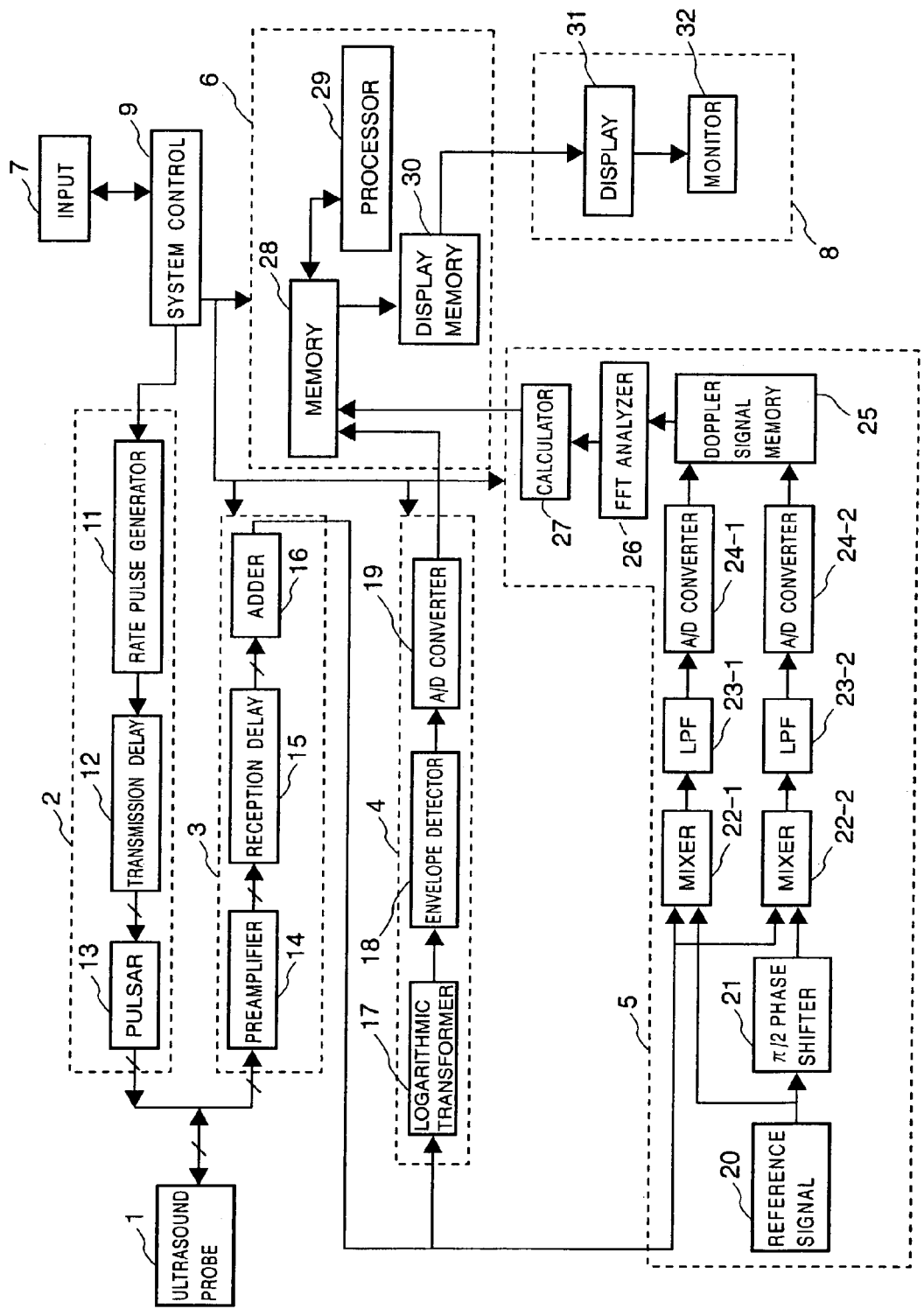
FIG. 2 is a block diagram showing an exemplary configuration of an ultrasound diagnosis apparatus according to a first embodiment of the present invention.

FIG. 2 is a block diagram showing an exemplary configuration of an ultrasound diagnosis apparatus according to the first embodiment of the present invention. The ultrasound diagnosis apparatus may include an ultrasound probe 1, an ultrasound transmission unit 2, an ultrasound reception unit 3, a B-mode processing unit 4, a Doppler-mode processing unit 5, an image measurement unit 6, an input unit 7, a display unit 8, and a system control unit 9.

The ultrasound probe 1 may transmit (or insonify) ultrasound pulses and receive echo signals from the specimen, resulting from the transmitted ultrasound pulses while the ultrasound probe is contacting with a body surface of the specimen. The ultrasound probe 1 includes a top end comprising a plurality of ultrasound micro-transducers arrayed in one dimension. The micro-transducers are electro-acoustic transducer elements. The micro-transducers convert electronic pulses into ultrasound pulses in transmission. Further, the micro-transducers convert ultrasound pulses into electronic pulses in reception. The ultrasound probe 1 is usually configured to be compact and lightweight, and is connected to the ultrasound transmission unit 2 and the ultrasound reception unit 3 through a cable. An operator may be able to select a type of the ultrasound probe 1 according to a part to be diagnosed among, for example, a sector scan, a linear-sector scan, and a convex scan. In the following description, the ultrasound probe 1 will be described about an example of a use for the sector scan.

The ultrasound transmission unit 2 may produce driving signals for generating the ultrasound pulses. The ultrasound transmission unit 2 may include a rate pulse generator 11, a transmission delay circuit 12, and a pulsar 13. The rate pulse generator 11 generates rate pulses, which determine repeated cycles of the ultrasound pulses insonified to the body of the specimen. The generated rate pulses are supplied to the transmission delay circuit 12. The transmission delay circuit 12 is a delay circuitry, which determines a convergent distance and a deflecting angle of an ultrasound beam in transmission. Further, the transmission delay circuit 12 may include a plurality of independent delay circuits. The number of the independent delay circuits to be used may be determined to be the same as that of the ultrasound transducers to be used in transmission. The transmission delay circuit 12 provides the generated rate pulses with a delay time for making the ultrasound pulses converge to a predetermined depth. This is for obtaining a narrow width of the ultrasound beam in transmission. The transmission delay circuit 12 further provides the generated pulses with another delay time for transmitting the ultrasound pulses in a predetermined direction. The delayed rate pulses are supplied to the pulsar 13. The pulsar 13 is a driving circuitry, which produces high voltage pulses for driving the ultrasound transducers. The pulsar 13 may include a plurality of independent driving circuits. The number of the independent driving circuits to be used may be determined to be the same as that of the ultrasound transducers to be used in the transmission as similar to the transmission delay circuit 12.

The ultrasound reception unit 3 may receive the ultrasound echo signals from the specimen. The ultrasound echo signals result from the ultrasound pulses insonified to the specimen. The ultrasound reception unit 3 may include a preamplifier 14, a reception delay circuit 15, and an adder 16. The preamplifier 14 amplifies small signals converted into the electronic pulses by the ultrasound transducers and obtains the electronic pulses, which has a preferable 'signal to noise' (S/N) rate. The reception delay circuit 15 gives output signals of the preamplifier 14 a delay time for converging the ultrasound echo signals from a predetermined depth (the output signals) so as to obtain a narrow width of an ultrasound beam in reception. The reception delay circuit 15 further gives the output signals another delay time for sequentially deflecting the ultrasound beam in a predetermined direction and scanning within the specimen. The reception delay circuit 15 supplies the adder 16 with the output signals given both the above delay time and the above another delay time. The adder 16 adds a plurality of the output signals and, accordingly, the plurality of the output signals are output as one ultrasound data signal.

The B-mode processing unit 4 may process the one ultrasound data signal so as to prepare a B-mode image data. The B-mode processing unit 4 may include a logarithmic transformer 17, an envelope detector 18, and an analog-to-digital converter (hereinafter referred to as an A/D converter) 19. The logarithmic transformer 17 performs a logarithmic transformation on an amplitude of the one ultrasound data signal so as to emphasize week elements of the one ultrasound data signal in comparison. In general, signals received from the insonified specimen have an amplitude with a wide dynamic range of more than 80 dB. Therefore, in order to display the signals received from the insonified specimen in a regular TV monitor with a narrow dynamic range, it is necessary to perform an amplitude compression on the signals so as to emphasize the weak elements of the signals. The envelope detector 18 detects envelopes of the one ultrasound data signal on which the logarithmic transformation has already been performed. The envelope detector 18 further removes ultrasonic frequency components of the envelope-detected signal and detects only an amplitude of the signal, which has been removed the ultrasonic frequency components. The A/D converter 19 converts an output signal of the envelope detector 18 into a digital signal. The digital signal represents a B-mode signal.

The Doppler-mode processing unit 5 may process the one ultrasound data signal so as to prepare a color Doppler image data or a tissue Doppler image data. The Doppler-mode processing unit 5 may include a reference signal generator 20, a $\pi/2$ phase shifter 21, mixers 22-1 and 22-2, low-pass filters 23-1 and 23-2, A/D converters 24-1 and 24-2, a Doppler signal memory 25, a fast Fourier transformation (hereinafter referred to as an FFT) analyzer 26, and a calculator 27. The Doppler-mode processing unit 5 primarily performs a quadrature demodulation and an FFT analysis.

The one ultrasound data signal is input to a first input terminal of the mixer 22-1 and also to a first input terminal of the mixer 22-2. The reference signal generator 20 has a frequency, which is nearly the same as that of the one ultrasound data signal. The reference signal generator 20 outputs a reference signal, which is directly supplied to a second terminal of the mixer 22-1. The reference signal is also supplied to the $\pi/2$ phase shifter 21. The $\pi/2$ phase shifter 21 shifts a phase of the reference signal and supplies a second terminal of the mixer 22-2 with a $\pi/2$ shifted reference signal. Output signals of the mixers 22-1 and 22-2 are supplied to the low-pass filters 23-1 and 23-2. The low-pass filter 23-1 removes a sum component of between a frequency of the reference signal and a frequency of the one ultrasound data signal. Accordingly, a differential component of between the frequency of the reference signal and the frequency of the one ultrasound data signal is extracted by the low-pass filter 23-1. Similarly, the low-pass filter 23-2 removes a sum component of between a frequency of the $\pi/2$ shifted reference signal and the frequency of the one ultrasound data signal. Accordingly, a differential component of between the frequency of the $\pi/2$ shifted reference signal and the frequency of the one ultrasound data signal is extracted by the low-pass filter 23-2.

The A/D converter 24-1 converts an output of the low-pass filter 23-1 into a digital signal. Similarly, the A/D converter 24-2 converts an output of the low-pass filter 23-2 into a digital signal. In other words, outputs resulting from a quadrature demodulation are converted into digital signals by the A/D converters 24-1 and 24-2. The digitized outputs resulting from the quadrature demodulation are temporarily stored in the Doppler signal memory 25 before supplied to the FFT analyzer 26. The FFT analyzer 26 performs the FFT analysis on the digitized outputs. The calculator 27 calculates a center, an expansion, and the like, of a spectrum obtained from the FFT analyzer 26.

The image measurement unit 6 may adjust time phases of two or more kinds of sequential images acquired under different conditions, respectively. In the following description, two kinds of sequential images will be described for explaining the first embodiment of the present invention. However, the number of (kinds of) sequential images may not be limited to only two.

The image measurement unit 6 may include a memory 28, a processor 29, and a display memory 30. The memory 28 may include an image memory and an auxiliary memory.

The image memory stores image data. The auxiliary memory stores measurement data, such as a volume, a diameter, and the like, of a heart chamber. To be more in detail, the image memory may store sequential image data, which have been acquired before their time phases are adjusted. The image memory may further store sequential image data, which have been acquired after their time phases have been adjusted. The auxiliary memory may store volume data obtained from the sequential image data, which have been acquired before their time phases are adjusted. The auxiliary memory may further store volume data obtained from the sequential image data, which have been acquired after their time phases have been adjusted. By the way, the image memory may store B-mode image data, Doppler-mode image data, and image data synthesizing the B-mode image data and the Doppler-mode image data, as sequential image data of the heart. In general, however, the B-mode image data may be used for the volume measurement of the heart chamber.

The processor 29 sequentially reads out each image of the two kinds of sequential image data stored in the memory 28 and measures a volume of a heart chamber included in the each image. Further, the processor 29 calculates a time-series volume transition of each of the two kinds of sequential image data. In each time-series volume transition, the processor 29 determines one or more peaks of the transition (greatest values) and one or more valleys of the transition (lowest values). Accordingly, the processor 29 determines a systolic period and a diastolic period of the heart based on the determined peaks and valleys. After the determination of the periods, the processor 29 compares the number of images included in the systolic period of one sequential image data and the number of images included in the systolic period of another sequential image data. Similarly, the processor 29 compares the number of images included in the diastolic period of one sequential image data and the number of images included in the diastolic period of another sequential image data. Based on the above comparison, the processor 29 adjusts time phases of the one sequential image data and the another sequential image data. For measuring (or calculating) the volume of the heart chamber, the heart chamber may be extracted by means of an Automated-Contour-Tracking (hereinafter referred to as an ACT) method. In addition, a Modified-Simpson technique may be used for the measurement calculation.

The auxiliary memory in the memory 28 stores the volume data calculated by the processor 29 and various measurement data, such as diameters of the heart chamber, calculated during processes for obtaining the volume data. The processor 29 may also measure a volume of the heart chamber, using the time phase adjusted two kinds of sequential image data, as a final measurement result for a diagnosis.

The display memory 30 temporarily stores images to be displayed in the display unit 8 and data, such as a chart showing the time-series volume transition and the like, to be displayed in the display unit 8. Images, such as B-mode images and/or Doppler-mode images, obtained in real time are temporarily stored in the display memory 30 and then displayed in the display unit 8.

The input unit 7 may have a keyboard, a trackball, a mouse, and the like, on an operation panel. The operator may operate the input unit 7 so as to input or select specimen information and imaging (or scanning) conditions of the ultrasound diagnosis apparatus. The conditions may include, for example, the number of images to be acquired in a unit time, a period or an interval for acquiring one sequential image data, and/or any other possible conditions relating to image acquisition and measurement.

The display unit 8 may include a display circuit 31 and a monitor 32. The system control unit 9 controls the display memory 30 to read out the sequential image data, which have been acquired before their time phases are adjusted, the sequential image data, which have been acquired after their time phases have been adjusted, data of the time-series volume transition of the heart chamber, and the like. The display circuit 31 converts the read-out data to digital signals and also to a TV format. The converted data are displayed in the monitor 32.

The system control unit 9 may include a central processing unit (hereinafter referred to as a CPU) and a memory. The system control unit 9 may control the ultrasound transmission unit 2, the ultrasound reception unit 3, the B-mode processing unit 4, the Doppler-mode processing unit 5, the image measurement unit 6, and the like. The system control unit 9 may also control over the ultrasound diagnosis apparatus. Particularly, when the operator operates the input unit 7, various command signals according to the operation are supplied to the CPU. Further, various kinds of control data tentatively determined at the time of shipment are stored in the memory 28 as initial data. Conditions supplied from the input unit 7 by the operator may also be stored in the memory 28.

Figure 3:
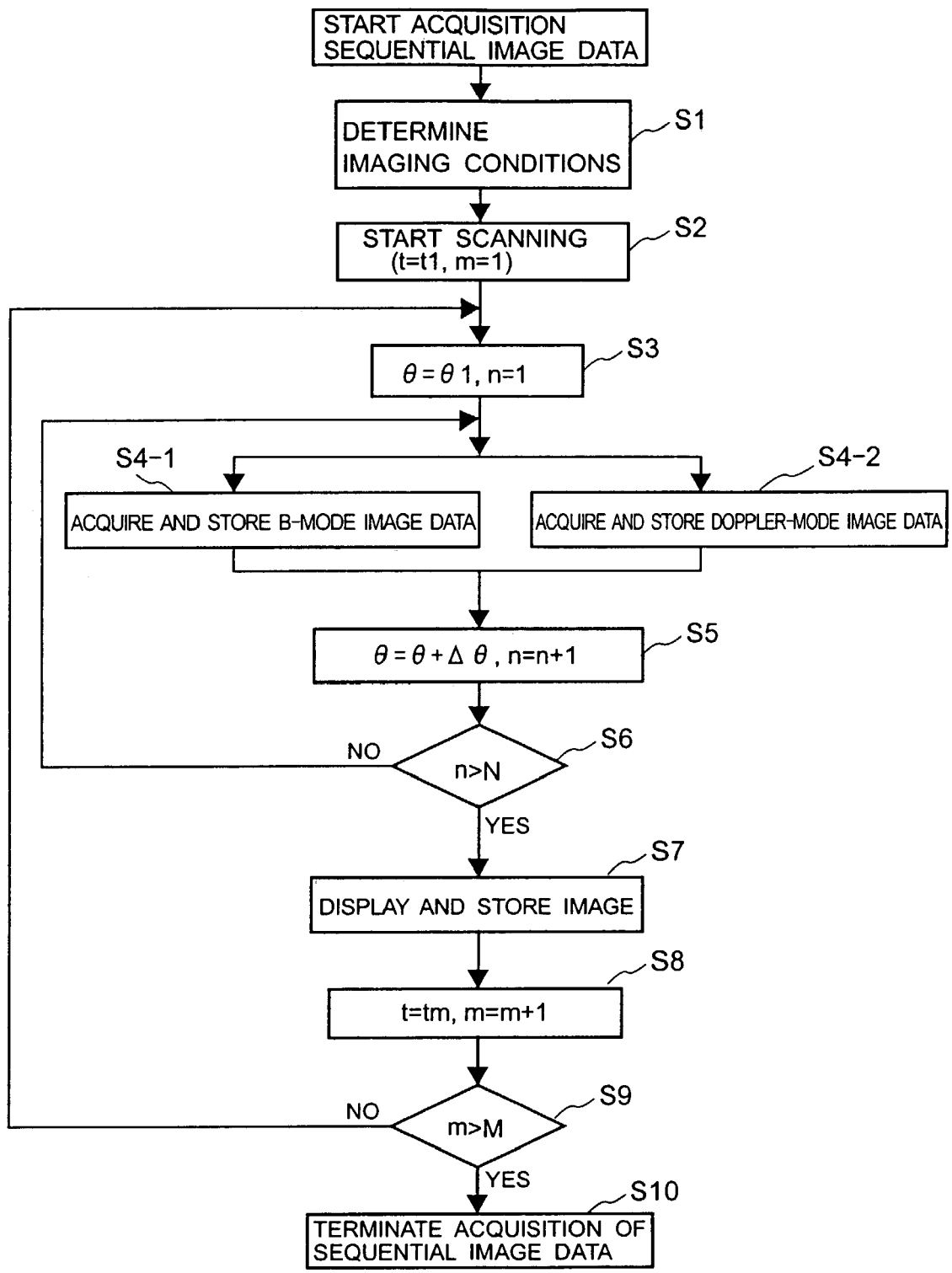
FIG. 3 is a flowchart showing an example of procedures for acquiring sequential image data according to the first embodiment of the present invention.

Next, procedures for acquiring sequential image data according to the first embodiment of the present invention will be described with reference to FIGS. 2 and 3. It should be noted that FIG. 3 shows procedures for acquiring sequential image data under only one condition (i.e., procedures for acquiring only one kind of sequential image data). Sequential image data under another condition can be acquired in a manner similar to the procedures shown in FIG. 3. FIG. 3 is a flowchart showing an example of procedures for acquiring sequential image data according to the first embodiment of the present invention.

Prior to image acquisition, the operator may operate the input unit 7 and choose an ultrasound probe to use as the ultrasound probe 1. The operator may also operate the input unit 7 and determine various imaging conditions, such as conditions of the ultrasound diagnosis apparatus, a period or an interval for acquiring one sequential image data, and the number of images (or frames) to be acquired in a unit time. The determined conditions are sent to and stored in the memory of the system control unit 9 (step S1). According to the first embodiment of the present invention, a sector probe for heart may be chosen as the ultrasound probe 1 and acquires four-chamber view sequential image data and two-chamber view sequential image data. An acquisition interval of each sequential image data may be, for example, determined to be equivalence of a couple of heartbeats. After such a determination, an imaging mode is automatically set up in the ultrasound diagnosis apparatus in accordance with the determined conditions.

The operator may fix the ultrasound probe 1 to a part of the specimen's body appropriate for imaging the four-chamber view of the heart. Accordingly, a scan is initiated for acquiring first (m=1) image data of the four-chamber view. The first image data may be obtained at a predetermined time (t=t1) (step S2). In practice, the operator may be likely to observe two-dimensional image data displayed in the monitor 32 and determine an appropriate position to fix the ultrasound probe 1. The observation may be enabled in a manner similar to the following steps of the procedures shown in FIG. 3.

In the ultrasound transmission, the rate pulse generator 11 synchronizes control signals supplied from the system control unit 9. The rate pulse generator 11 generates rate pulses, which determine repeated cycles of the ultrasound pulses insonified to the body of the specimen. The generated rate pulses are supplied to the transmission delay circuit 12. The transmission delay circuit 12 is a delay circuitry, which determines a convergent distance and a deflecting angle of an ultrasound beam in transmission. Further, the transmission delay circuit 12 may include a plurality of independent delay circuits. The number of the independent delay circuits to be used may be determined to be the same as that of the ultrasound transducers to be used in transmission. The transmission delay circuit 12 provides the generated rate pulses with a delay time for making the ultrasound pulses converge to a predetermined depth. This is for obtaining a narrow width of the ultrasound beam in transmission. The transmission delay circuit 12 further provides the generated rate pulses with another delay time for transmitting the ultrasound pulses in a predetermined direction ($\theta:\theta=\theta 1$). The transmission will be made in N directions for acquiring the first image data (Ix1). The above direction $\theta 1$ is only a first (n=1) direction. The delayed rate pulses are supplied to the pulsar 13.

The pulsar 13 may include a plurality of independent driving circuits. The number of the independent driving circuits to be used may be determined to be the same as that of the ultrasound transducers to be used in the transmission as similar to the transmission delay circuit 12. The pulsar 13 drives the ultrasound transducers provided in the ultrasound probe 1 by pulses for driving the ultrasound transducers generated responsive to driving rate pulses. Accordingly, the ultrasound pulses are insonified to an inside of the specimen's body. Part of the ultrasound waves insonified to the specimen's body usually reflects off tissues or borders between organs within the specimen's body, where their acoustic impedances are different. Further, when the part of the ultrasound waves reflects off moving reflectors, such as blood cells and heart walls, its ultrasound frequencies are subjected to Doppler-shifts. received signals another delay time for receiving the ultrasound beam with strong directional characteristics for a predetermined direction ($\theta=\theta 1$). The reception delay circuit 15 supplies the adder 16 with the received signals given both the above delay time and the above another delay time. The received signals are supplied to the adder 16 from the reception delay circuit 15. The adder 16 adds (or unifies) a plurality of the received signals supplied through the preamplifier 14 and the reception delay circuit 15. Accordingly, the plurality of the received signals are output to the B-mode processing unit 4 and the Doppler-mode processing unit 5 as one ultrasound data signal (step 3).

In the B-mode processing unit 4, the logarithmic transformer 17 performs the logarithmic transformation on the one ultrasound data signal. The envelope detector 18 detects envelopes of the one transformed ultrasound data signal. The one detected ultrasound data signal is converted into a digital signal by the A/D converter 19. The digital signal is sent to the display memory 30 through the memory 28 and stored in the display memory 30 as a first-direction B-mode image data (step S4-1).

In the Doppler-mode processing unit 5, the quadrature demodulation is performed on the one ultrasound data signal. The demodulated signal is converted to a complex signal through the mixers 22-1 and 22-2 and the low-pass filter 23-1 and 23-2. The complex signal is converted into a digital signal by the A/D converters 24-1 and 24-2 and is stored in the Doppler signal memory 25. For the Doppler-mode processing, the scanning by insonifying the ultrasound waves may be performed in the same direction (θ1) several times. As a result, a plurality of received signals are obtained. For each of the received signals, the processing described above is performed, and accordingly, a plurality of digital complex signals are stored in the Doppler signal memory 25. The FFT analyzer 26 obtains frequency spectrums based on the plurality of digital complex signals stored in the Doppler signal memory 25, respectively. The calculator 27 calculates and determines a center (i.e., an average speed of an organ movement and/or a blood stream) of the frequency spectrums. A result of the calculation is sent to the display memory 30 through the memory 28 and stored in the display memory 30 as first direction Doppler-mode image data (step S4-2).

After the storage in steps S4-1 and S4-2, the predetermined direction θ is changed to a second predetermined direction in a manner following a formula (θ=θ+Δθ). Since the predetermined direction was θ1, the second predetermined direction (θ) becomes θ1+Δθ. The 'n' indicating the number of scanning directions is also increased one by one (n=n+1). Therefore, the second predetermined direction (θ1+Δθ) becomes a second (n=2) direction (step S5). The processing described in steps S4-1, S4-2, and S5 is repeated until the 'n' becomes N (step S6) so that the scanning is performed in N predetermined directions (from the predetermined direction (θ1) to an $N^{th}$ predetermined direction (θ1+(N−1)Δθ)). The scanning in the N directions is performed for the specimen's body in real time by insonifying the ultrasound waves and receiving the ultrasound echo signals. During the scanning, the system control unit 9 controls the transmission delay circuit 12 and the reception delay circuit 15 to change their delay times in accordance with the N predetermined directions. For the N directions, N directions B-mode image data and N directions Doppler-mode image data are acquired in steps S4-1 and S4-2.

The system control unit 9 controls to sequentially store, the N directions B-mode image data and the N directions Doppler-mode image data acquired in steps S4-1 and S4-2, in the display memory 30. When the N-direction scanning has been completed, first B-mode image (or frame) data (Ixm=Ix1) is produced based on the N directions B-mode image data. Further, first Doppler-mode image (or frame) data is produced based on the N directions Doppler-mode image data. Still further, first synthesized image data is produced based on the first B-mode image data Ix1 and the first Doppler-mode image data. The first synthesized image data is displayed as a first synthesized image in the monitor 32 through the display circuit 31. The first B-mode image data Ix1, the first Doppler-mode image data, and the first synthesized image data are stored in the memory 28 (step S7). The first B-mode image data Ix1 and/or the first Doppler-mode image data may also be displayed in the monitor 32.

After the display and the storage of the first synthesized image data, procedures for second synthesized image data will be prepared by updating the image number 'm' (m=m+1) so that the second synthesized image data, as well as second B-mode image data (Ixm=Ix2) and second Doppler-mode image data, of the four-chamber view will be acquired at a predetermined time (t=tm=t2) (step S8).

The procedures described in steps S3 to S8 will be repeated until further acquisition of synthesized image data as well as second B-mode image data and second Doppler-mode image data. After the $M^{th}$ synthesized image data has acquired, the image number 'm' is increased one again in step S8 and becomes 'M+1' (m=M+1). This is determined in step S9. Accordingly, M synthesized image data (hereinafter referred to as first sequential image data) as well as M B-mode image data (hereinafter referred to as first sequential B-mode image data) (Ix1 to IxM) and M Doppler image data (hereinafter referred to as first sequential Doppler-mode image data) are acquired during a period between the predetermined time t1 and the predetermined time tM. The period may include a period of a couple of heartbeats (at least two heartbeats corresponding to two R waves). The number of images to be acquired between two R waves may usually be around 30 to 100. The first sequential image data are sent to the monitor 32 through the display memory 30 and the display circuit 31. In the monitor 32, the first sequential image data are sequentially displayed in real time as first sequential images. The first sequential B-mode image data (Ix1 to IxM), the first sequential Doppler-mode image data, and the first sequential image data are stored in the memory 28. The first sequential B-mode image data (Ix1 to IxM) and/or the first sequential Doppler-mode image data may also be displayed in the monitor 32. Responsive to the storage, the ultrasound imaging of the four-chamber view of the heart is terminated (step S10).

For the two-chamber view of the heart, image data may be acquired in accordance with procedures similar to those explained in FIG. 3. For the two-chamber view of the heart, the operator may need to turn the ultrasound probe 1 approximately 90 degrees around an axis of the ultrasound probe 1 from the position fixed for the four-chamber view and, if necessary, also slightly adjust the position against the body surface of the specimen, the angle, and/or the direction of the ultrasound probe 1. The system control unit 9 controls each unit of the ultrasound diagnosis apparatus to obtain a plurality of B-mode image data, a plurality of Doppler-mode image data, and a plurality of synthesized image data, regarding the two-chamber view. When, for example, the number of the B-mode image data is the same as that (M) of the first sequential B-mode image data, M B-mode image data may be defined as second sequential B-mode image data (Iy1 to IyM) in a manner similar to the first sequential B-mode image data (Ix1 to IxM). The number of the B-mode image data may alternatively be different from that of the first sequential B-mode image data, in some cases. The number of the Doppler-mode image data may be the same as that (M) of the second sequential B-mode image data. M Doppler-mode image data may hereinafter be referred to as second sequential Doppler-mode image data. Further, the number of the synthesized image data may be the same as that (M) of the second sequential B-mode image data. M synthesized image data may hereinafter be referred to as second sequential image data. The second sequential image data are sent to the monitor 32 through the display memory 30 and the display circuit 31. In the monitor 32, the second sequential image data are sequentially displayed in real time as second sequential images. The second sequential B-mode image data (Iy1 to IyM), the second sequential Doppler-mode image data, and the second sequential image data are stored in the memory 28. The second sequential B-mode image data (Iy1 to IyM) and the second sequential Doppler-mode image data may also be displayed in the monitor 32. Responsive to the storage, the ultrasound imaging of the two-chamber view of the heart is terminated.

Figure 4:
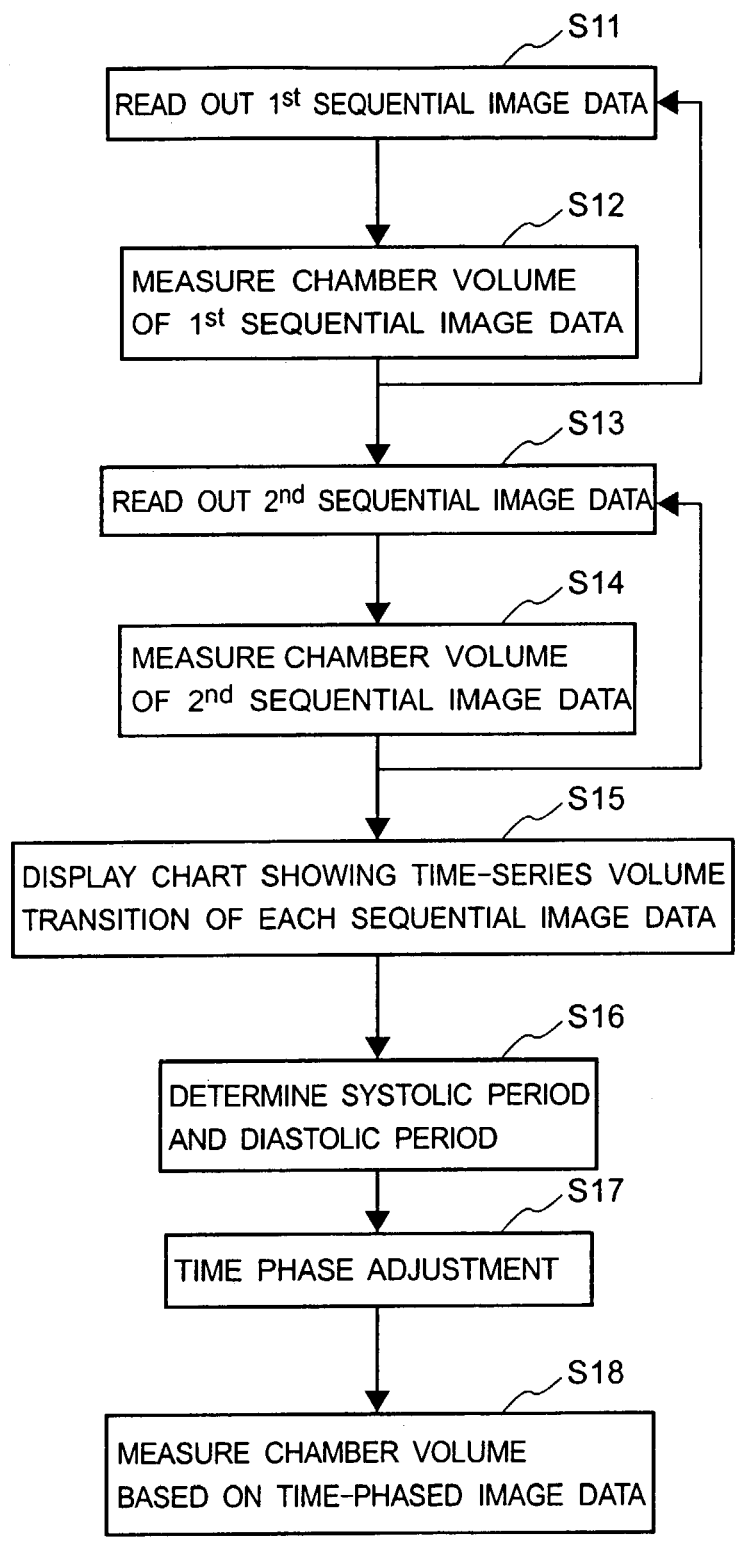
FIG. 4 is a flowchart showing an example of procedures for a time phase adjustment according to the first embodiment of the present invention.
Figure 5B:
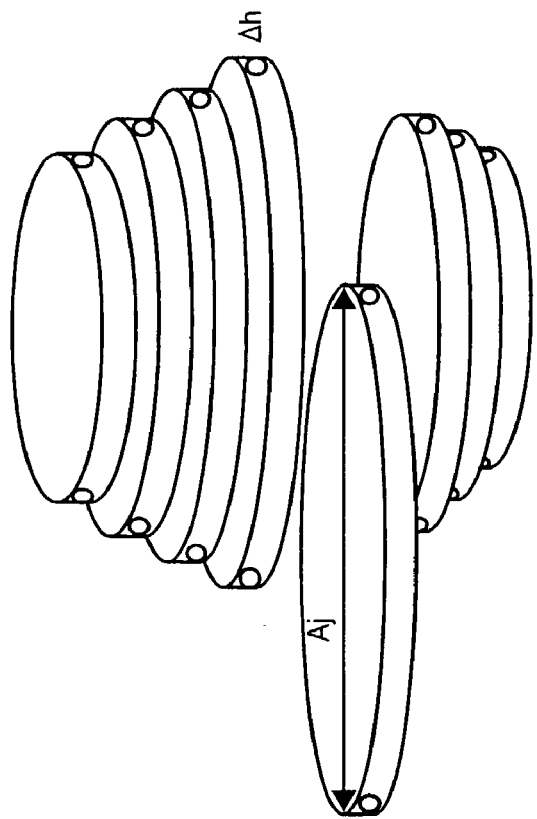
FIG. 5B is an illustration showing an example of column models regarding the volume measurement of the heart chamber according to the first embodiment of the present invention.
Figure 5A:
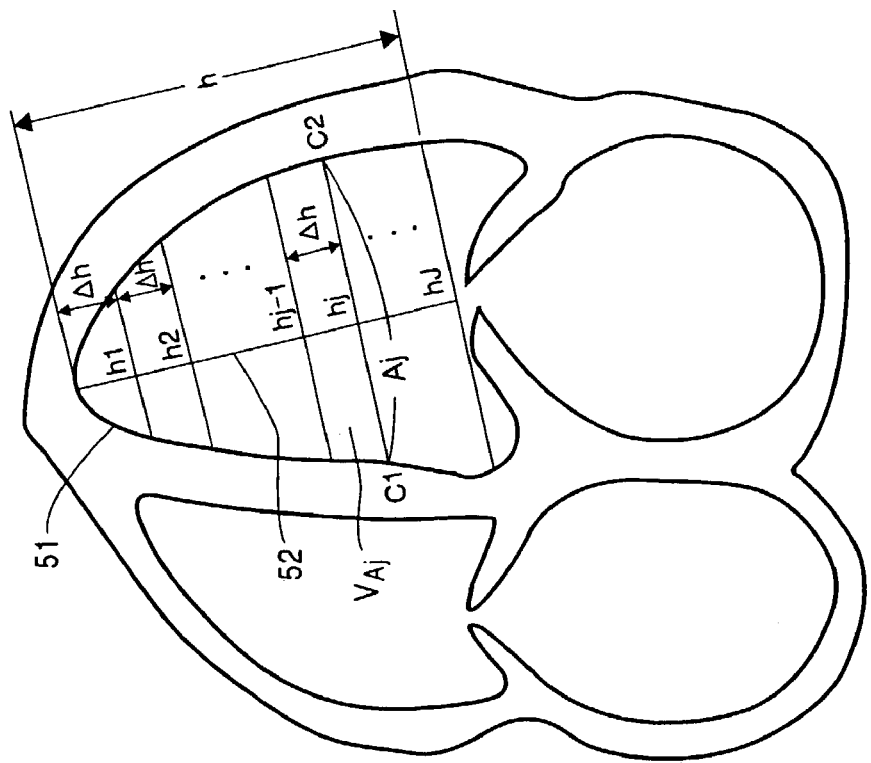
FIG. 5A is an illustration showing an example of sequential B-mode image data for explaining a volume measurement of a heart chamber according to the first embodiment of the present invention.

When two kinds of sequential image data (the first sequential image data and the second sequential image data) have been obtained, the processor 29 will start to adjust a time phase of the first sequential image data (hereinafter referred to as a first time phase) and a time phase of the second sequential image data (hereinafter referred to as a second time phase) based on volume measurements of the chambers. Such a time phase adjustment will be described with reference to FIGS. 2 and 4 to 7. FIG. 4 is a flowchart showing an example of procedures for a time phase adjustment according to the first embodiment of the present invention. FIG. 5A is an illustration showing an example of one of the first sequential B-mode image data for explaining the volume measurement of the heart chamber according to the first embodiment of the present invention. FIG. 5B is an illustration showing an example of column models regarding the volume measurement of the heart chamber according to the first embodiment of the present invention. In more detail, FIG. 5A shows an example of a volume measurement technique of a left ventricle shown in the four-chamber view of the heart in the one of the first sequential images according to the first embodiment of the present invention.

The processor 29 reads out first B-mode image data Ix1 of the four-chamber view from the first sequential B-mode image data (Ix1 to IxM) stored in the memory 28 (step S11). The processor 29 uses a contour extraction technique to extract a heart chamber (e.g., a left ventricle) lining in the first B-mode image data Ix1. For example, the heart chamber lining may be extracted by the processor 29, using the ACT method. The ACT method is already known, for example, in an article included in a document called 'Medical Review No. 71' published in 1988. The article (pages 50–54 of the document) was written by Nishiura et al. and entitled 'Automatic Extraction of Ultrasound Heart Wall Contour, Using an ACT Technique' (informal translation). As shown in FIG. 5A, the processor 29 extracts a contour 51 of the heart chamber lining in accordance with the ACT method and accordingly detects a mitral annulus from the extracted contour. Further, the processor 29 determines a long axis 52 in the longitudinal direction of the heart chamber based on the mitral annulus. When a height of the heart chamber lining along the long axis 52 is h, for example, a length of the long axis 52 is also h. The long axis 52 may be divided, at predetermined points hj (j=1 to J), into a predetermined number J (e.g., J=20) of line segments each of which has a same length $\Delta h$ ($\Delta h=h/J$). In this case, it may be possible to treat an internal space of the heart chamber as a gathering of the predetermined number J of blocks each of which has a same height $\Delta h$ along the long axis 52. When a line that is perpendicular to the long axis 52 at a predetermined point hj is drawn to the heart chamber lining, the perpendicular line intersects with the heart chamber lining at points C1 and C2. The processor 29 may calculate a length $A_j$ of the perpendicular line between the points C1 and C2. The length h, the length $A_j$, and any other related data mentioned above, if necessary, are stored in the auxiliary memory of the memory 28. One block j of the J blocks under the above condition may be assumed to be a column comprising the height $\Delta h$ The ultrasound waves reflected off the tissues of the specimen may be received as the ultrasound echo signals by the ultrasound transducers. In detail, each of the ultrasound echo signals may be received by each of the ultrasound transducers, which insonified an ultrasound wave resulting in the each ultrasound echo signal. The received ultrasound echo signals are converted into electronic signals. The converted electronic signals are amplified by the preamplifier 14. The preamplifier may include a plurality of amplifying elements. The number of the amplifying elements to be used may be determined to be the same as that of the ultrasound transducers to be used in the reception. The reception delay circuit 15 receives the preamplified signals.

In the reception delay circuit 15, the same number of delay circuits as the that of the used ultrasound transducers may be used for the reception.

The reception delay circuit 15 gives the received signals a delay time for converging the ultrasound echo signals from a predetermined depth (the received signals) so as to obtain a narrow width of an ultrasound beam in reception. The reception delay circuit 15 further gives the and a circular surface with a diameter $A_j$. Accordingly, a volume $V_{Aj}$ of the block j can be approximated by a formula:

$$V_{Aj} \Delta h \times \pi (A_j/2)^2$$

In this assumption, according to the Modified-Simpson technique known in this field, a volume Vx1 of the internal space can be approximated to a result of summing the volume $V_{Aj}$ on all the J blocks ($Vx1=V_{A1}+V_{A2}+\ldots+V_{AJ}$), as shown in FIG. 5B. This is represented with the following formula:

$$Vx1 = \sum V_{Aj} \; (j = 1 \text{ to } J) \hspace{2cm} (1)$$
$$= \sum \Delta h \times \pi (A_j/2)^2 \; (j = 1 \text{ to } J).$$

Details of the volume measurement (calculation) using the Modified-Simpson technique are described in an article included in a document called 'Echocardiography Vol. 2, No. 3' published in 2001. The article (pages 192–197 of the document) was written by Takeuchi et al. and entitled 'Accurate Measurement Technique of Heart Chamber Size, 2) Atriums' (NB. This is an informal translation.). Therefore, further detailed explanation of the calculation will be omitted herein.

Figure 6:
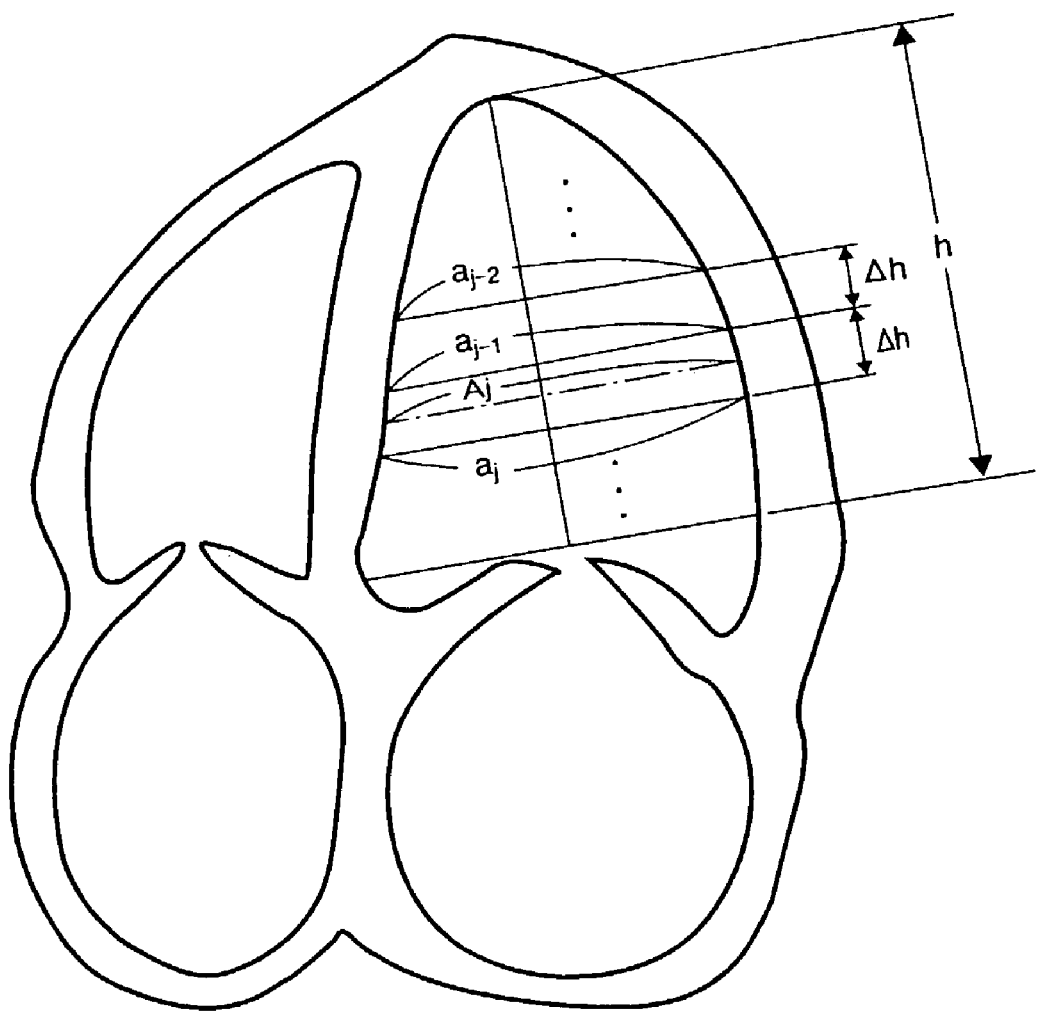
FIG. 6 is an illustration showing an example of sequential B-mode image data for explaining the volume measurement of the heart chamber in more detail according to the first embodiment of the present invention.

FIG. 6 is an illustration showing an example of one of the second sequential B-mode image data for explaining the volume measurement of the heart chamber more in detail according to the first embodiment of the present invention. As understood in FIG. 6, in order to obtain a more correct volume of the internal space, the diameter $A_j$ described above may be calculated as follows.

The one block j of the J blocks may usually not be a complete column. In other words, the one block j may have a lower surface assumed to be a circle with a diameter $a_j$ (j=1 to J) and an upper surface assumed to be a circle with a diameter $a_{j-1}$. When 'j' represents an odd number, the diameter $a_j$ is a diameter of a surface which comes in an odd-numbered order while the diameter $a_{j-1}$ is a diameter of a surface which comes in an even-numbered order. Similarly, when 'j' represents an even number, the diameter $a_j$ is a diameter of a surface which comes in an even-numbered order while the diameter $a_{j-1}$ is a diameter of a surface which comes in an odd-numbered order. As described above, the height of the one block j may be defined as $\Delta h$ ($\Delta h=h/J$). Therefore, if one takes a diameter ($A_j$) at the height $\Delta h/2$ of the one block j as each of an approximated diameter of the lower surface and an approximated diameter of the upper surface, the diameter $A_j$ may be represented as $(a_{j-1}+a_j)/2$. This means that the one block j can be assumed to be a column, which comprises the height $\Delta h$ and a circular surface with a diameter $A_j$ ($A_j=(a_{j-1}+a_j)/2$). Therefore, the formula (1) can be replaced with the following formula (2):

$$Vx1 \Sigma \Delta h \times \pi(((a_{j-1}+a_j)/2)/2)^2 \; (j=1 \text{ to } J) \hspace{2cm} (2).$$

Since the height Δh has been defined as Δh=h/J, the volume Vx1 in the formula (2) can be further rewritten as the following formula (3):

$$Vx1 = (\pi h/16)\Sigma(a_{j-1}+a_j)^2 \quad (j=1 \text{ to } J) \tag{3}$$

The processor 29 sends the volume Vx1 calculated in the above calculation to the memory 28. In the memory 28, the volume Vx1 is stored in the auxiliary memory (step S12).

After the volume calculation (or measurement) for the first B-mode image data Ix1 of the four-chamber view included in the first sequential B-mode image data (Ix1 to IxM), the second B-mode image data Ix2 is read out from the memory 28 by the processor 29. Again, the processor 29 uses a contour extraction technique to extract a heart chamber lining in the second B-mode image data Ix2. The heart chamber for its lining extraction in the second B-mode image data Ix2 is the same as that in the first B-mode image data Ix1. A volume Vx2 of an internal space of the heart chamber is obtained in a manner similar to the calculation of the volume Vx1 in the first B-mode image data Ix1. Repeating similar procedures, the processor 29 obtains volumes Vx3 to VxM for the third to the M$^{th}$ B-mode image data. The volumes Vx2 to VxM are stored in the auxiliary memory of the memory 28, respectively, as each of the volumes Vx2 to VxM is obtained (steps S11 to S12).

The processor 29 then reads out first B-mode image data Iy1 of the two-chamber view from the second sequential B-mode image data (Iy1 to IyM) stored in the memory 28 (step S13). The processor 29 uses a contour extraction technique to extract a heart chamber lining in the first B-mode image data Iy1. The heart chamber for its lining extraction in the second sequential B-mode image data (Iy1 to IyM) is the same as that in the first sequential B-mode image data (Ix1 to IxM).

For example, the heart chamber lining may be extracted by the processor 29, using the ACT method. As described for the first sequential B-mode image data (Ix1 to IxM), the processor 29 extracts a contour of the heart chamber lining in accordance with the ACT method and accordingly detects a mitral annulus from the extracted contour. Further, the processor 29 determines a long axis in the longitudinal direction of the heart chamber based on the mitral annulus. When a height of the heart chamber lining along the long axis is h, for example, a length of the long axis is also h. The long axis may be divided, at predetermined points hj (j=1 to J), into the predetermined number J of line segments each of which has a same length Δh (Δh=h/J). In this case, it may also be possible to treat an internal space of the heart chamber as a gathering of the predetermined number J of blocks each of which has a same height Δh along the long axis. When a line that is perpendicular to the long axis at a predetermined point hj is drawn to the heart chamber lining, the perpendicular line intersects with the heart chamber lining at two points. The processor 29 may calculate a length Bj of the perpendicular line between the two points. The length h, the length Bj, and any other related data mentioned above, if necessary, are stored in the auxiliary memory of the memory 28. One block j of the J blocks under the above condition may be assumed to be a column comprising the height Δh and a circular surface with a diameter Bj. Accordingly, a volume $V_{Bj}$ of the block j can be approximated by a formula:

$$V_{Bj} = \Delta h \times \pi (Bj/2)^2$$

In this assumption, according to the Modified-Simpson technique known in this field, a volume Vy1 of the internal space can be approximated to a result of summing the volume $V_{Bj}$ on all the J blocks (Vy1=$V_{B1}$+$V_{B2}$+ . . . +$V_{BJ}$). This is represented with the following formula:

$$Vy1 = \sum V_{Bj} \quad (j = 1 \text{ to } J) \tag{4}$$
$$= \sum \Delta h \times \pi (B_j/2)^2 \quad (j = 1 \text{ to } J).$$

Figure 7:
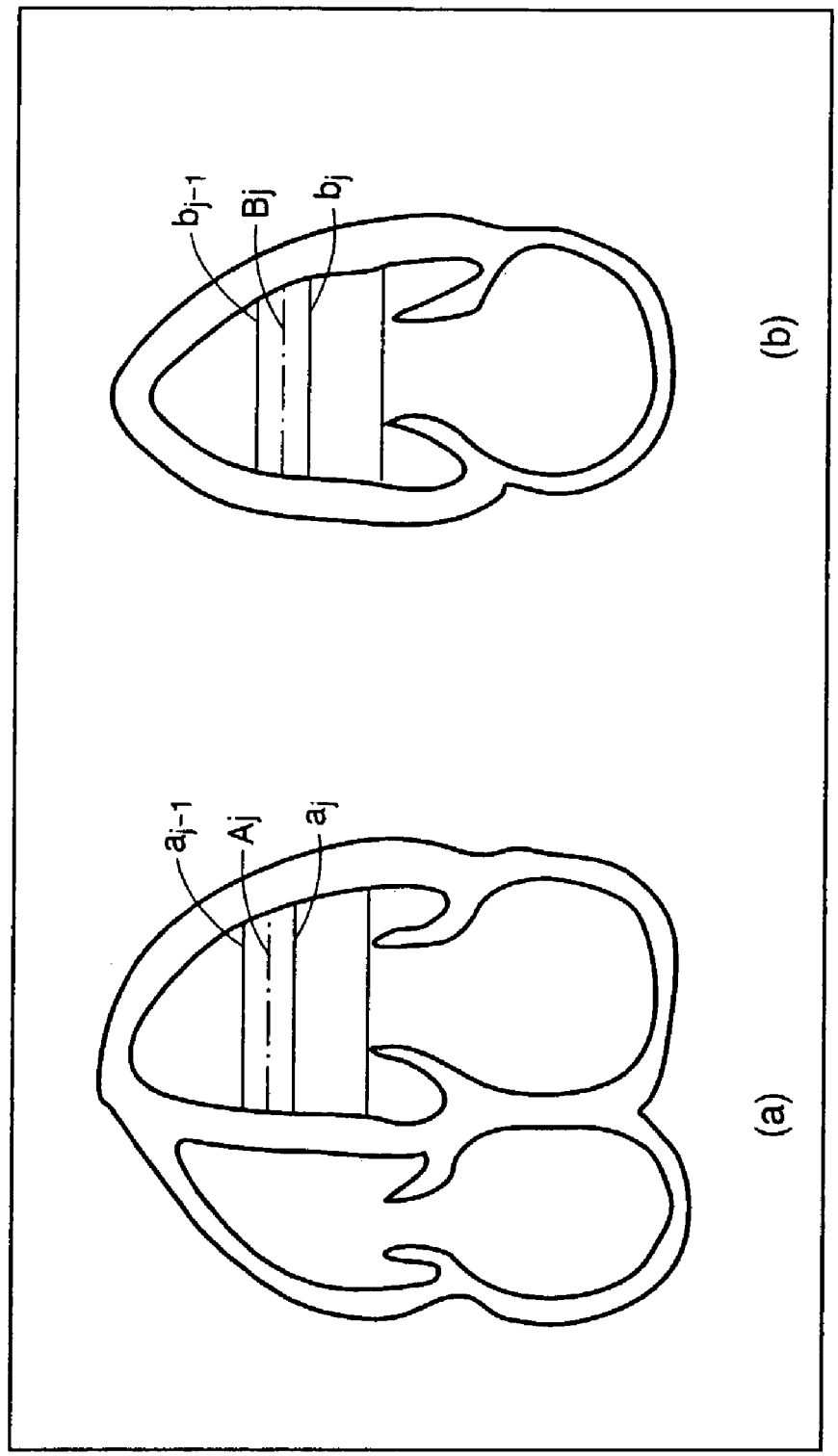
FIG. 7 is an illustration showing an example of each one of two kinds of sequential B-mode image data for explaining the volume measurement of the heart chamber according to the first embodiment of the present invention.

FIG. 7 is an illustration showing an example of each one of two kinds of sequential B-mode image data for explaining the volume measurement of the heart chamber according to the first embodiment of the present invention. FIG. 7(a) shows one of the first sequential B-mode image data. FIG. 7(b) shows one of the second sequential B-mode image data.

As similar to the first sequential B-mode image data, in order to obtain a more correct volume of the internal space, the diameter Bj described above may be calculated as follows.

The one block j of the J blocks may usually not be a complete column. In other words, the one block j may have a lower surface assumed to be a circle with a diameter $b_j$ (j=1 to J) and an upper surface with a diameter $b_{j-1}$, as shown in FIG. 7(b). When 'j' represents an odd number, the diameter $b_j$ is a diameter of a surface which comes in an odd-numbered order while the diameter $b_{j-1}$ is a diameter of a surface which comes in an even-numbered order. Similarly, when 'j' represents an even number, the diameter $b_j$ is a diameter of a surface which comes in an even-numbered order while the diameter $b_{j-1}$ is a diameter of a surface which comes in an odd-numbered order. As described above, the height of the one block may be defined as Δh (Δh=h/J). Therefore, if one takes a diameter (Bj) at the height Δh/2 of the one block j as each of an approximated diameter of the lower surface and an approximated diameter of the upper surface, the diameter Bj may be represented as $(b_{j-1}+b_j)/2$. This means that the one block j can be assumed to be a column, which comprises the height Δh and a circular surface with a diameter Bj (Bj=$(b_{j-1}+b_j)/2$). Therefore, the formula (4) can be replaced with the following formula (5):

$$Vy1 = \Sigma \Delta h \times \pi (((b_{j-1}+b_j)/2)/2)^2 \quad (j=1 \text{ to } J) \tag{5}$$

Since the height Δh has been defined as Δh=h/J, the volume Vy1 in the formula (5) can be further rewritten as the following formula (6):

$$Vy1 = (\pi h/16)\Sigma(b_{j-1}+b_j)^2 \quad (j=1 \text{ to } J) \tag{6}$$

The processor 29 sends the volume Vy1 calculated in the above calculation to the memory 28. In the memory 28, the volume Vy1 is stored in the auxiliary memory (step 14).

After the volume calculation (or measurement) for the first B-mode image data Iy1 of the two-chamber view included in the second sequential B-mode image data (Iy1 to IyM), the second B-mode image data Iy2 is read out from the memory 28 by the processor 29. Again, the processor 29 uses a contour extraction technique to extract a heart chamber lining in the second B-mode image data Iy2. The heart chamber for its lining extraction in the second B-mode image data Iy2 is the same as that in the first B-mode image data Iy1. A volume Vy2 of an internal space of the heart chamber is obtained in a manner similar to the calculation of the volume Vy1 in the first B-mode image data Iy1. Repeating similar procedures, the processor 29 obtains volumes Vy3 to VyM for the third to the M$^{th}$ B-mode image data. The volumes Vy2 to VyM are stored in the auxiliary memory of the memory 28, respectively, as each of the volumes Vy2 to VyM is obtained (steps S13 to S14).

After obtaining both the volumes (or volume data) Vx1 to VxM in the four-chamber view and Vy1 to VyM in the two-chamber view, the system control unit 9 controls to temporarily store the volumes Vx1 to VxM and Vy1 to VyM in the display memory 30. The stored volumes Vx1 to VxM and Vy1 to VyM are then displayed in the monitor 32 through the display circuit 31 in a form of a time-series volume transition (step S15).

Figure 8:
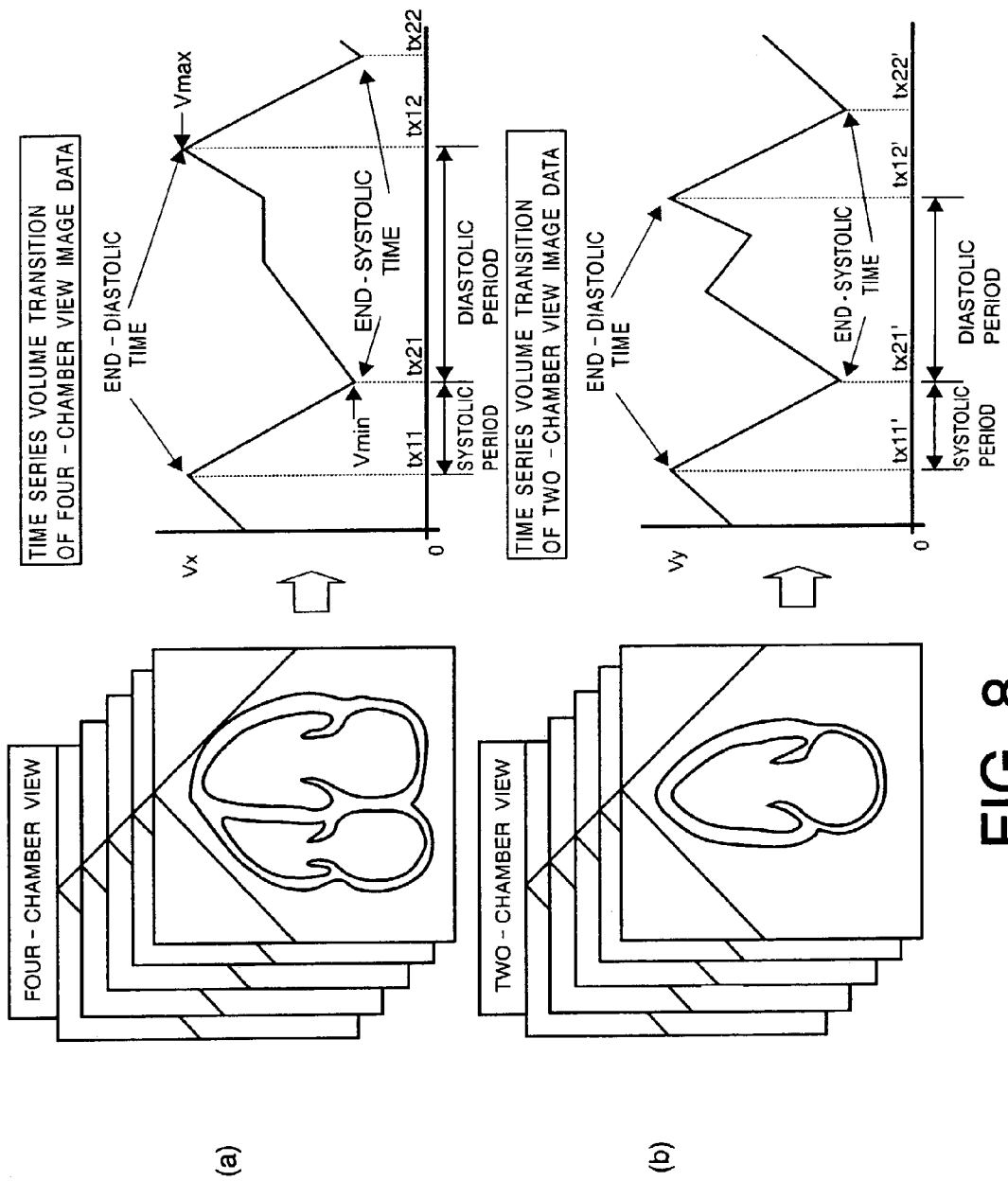
FIG. 8 is an illustration showing an example of a relationship between sequential image data and charts of time-series volume transitions according to the first embodiment of the present invention.

FIG. 8 is an illustration showing an example of a relationship between sequential image data and charts of time-series volume transitions according to the first embodiment of the present invention. FIG. 8(a) shows first sequential B-mode image data of the four-chamber view. FIG. 8(a) further shows a time-series volume transition chart of the first sequential B-mode image data. Similarly, FIG. 8(b) shows second sequential B-mode image data of the two-chamber view. FIG. 8(b) further shows a time-series volume transition chart of the second sequential B-mode image data. In the time-series volume transition chart in FIG. 8(a), volumes calculated by applying the formula (3) to each B-mode image data of the first sequential B-mode image data are plotted in time-series along acquisition of the first sequential B-mode image data. Similarly, in the time-series volume transition chart in FIG. 8(b), volumes calculated by applying the formula (6) to each B-mode image data of the second sequential B-mode image data are plotted in time-series along acquisition of the second sequential B-mode image data. The each B-mode image data of the first sequential B-mode image data may be acquired at an interval Tx. The each B-mode image data of the second sequential B-mode image data may be acquired at an interval Ty.

In the time-series volume transition chart shown in FIG. 8(a), a first peak at a time phase tx11 may be determined to be a first four-chamber end-diastolic time. The first peak is a time when the calculated volume Vx becomes greatest for the first time among the first sequential B-mode image data. Also a second peak at a time phase tx12 may be determined to be a second four-chamber end-diastolic time. The second peak is a time when the calculated volume Vx becomes greatest for the second time among the first sequential B-mode image data. On the other hand, a first valley at a time phase tx21 may be determined to be a first four-chamber end-systolic time. The first valley is a time when the calculated volume Vx becomes smallest for the first time among the first sequential B-mode image data. Also a second valley at a time phase tx22 may be determined to be a second four-chamber end-systolic time. The second valley is a time when the calculated volume Vx becomes smallest for the second time among the first sequential B-mode image data. A period between the first four-chamber end-diastolic time tx11 and the first four-chamber end-systolic time tx21 is determined to be a first four-chamber systolic period [tx11–tx21]. A period between the second four-chamber end-diastolic time tx12 and the second four-chamber end-systolic time tx22 is determined to be a second four-chamber systolic period [tx12–tx22]. In addition, a period between the first four-chamber end-systolic time tx21 and the second four-chamber end-diastolic time tx12 is determined to be a four-chamber diastolic period [tx21–tx12].

Similar to FIG. 8(a), in the time-series volume transition chart shown in FIG. 8(b), a first peak at a time phase tx11' may be determined to be a first two-chamber end-diastolic time. The first peak is a time when the calculated volume Vy becomes greatest for the first time among the second sequential B-mode image data. Also a second peak at a time phase tx12' may be determined to be a second two-chamber end-diastolic time. The second peak is a time when the calculated volume Vy becomes greatest for the second time among the second sequential B-mode image data. On the other hand, a first valley at a time phase tx21' may be determined to be a first two-chamber end-systolic time. The first valley is a time when the calculated volume Vy becomes smallest for the first time among the second sequential B-mode image data. Also a second valley at a time phase tx22' may be determined to be a second two-chamber end-systolic time. The second valley is a time when the calculated volume Vy becomes smallest for the second time among the second sequential B-mode image data. A period between the first two-chamber end-diastolic time tx11' and the first two-chamber end-systolic time tx21' is determined to be a first two-chamber systolic period [tx11'–tx21']. A period between the second two-chamber end-diastolic time tx12' and the second two-chamber end-systolic time tx22' is determined to be a second two-chamber systolic period [tx12'–tx22']. In addition, a period between the first two-chamber end-systolic time tx21' and the second two-chamber end-diastolic time tx12' is determined to be a two-chamber diastolic period [tx21'–tx12'].

In order to determine the times and the periods of the first sequential B-mode image data described above, the processor 29 reads out the first sequential B-mode image data Vx1 to VxM. The processor 29 detects one or more peak (or maximum) values Vmax of the volumes Vx1 to VxM and also one or more valley (or minimum) values Vmin of the volumes Vx1 to VxM. When the one or more peak (or maximum) values Vmax are detected, the processor 29 can recognize one or more B-mode image data which have the peak values Vmax. Accordingly, the processor 29 can determine the end-diastolic times, such as the first four-chamber end-diastolic time tx11 and the second four-chamber end-diastolic time tx12. Similarly, when the one or more valley (or minimum) values Vmin are detected, the processor 29 can recognize one or more B-mode image data which have the valley values Vmin. Accordingly, the processor can determine the end-systolic times, such as the first four-chamber end-systolic time tx21 and the second four-chamber end-systolic time tx22. The determination of the first and second four-chamber end-diastolic times tx11, tx12 and the first and second four-chamber end-systolic times tx21, tx22 leads to determination of the first and second four-chamber systolic periods [tx11–tx21], [tx12–tx22] and the four-chamber diastolic period [tx21–tx12]. Responsive to the determination of the periods, the processor 29 determines the number of the volume data (i.e., the number of the B-mode image data) included in each of the periods. This image number determination may substantially automatically be accomplished responsive to the period determination.

Similarly, in order to determine the times and the periods of the second sequential B-mode image data described above, the processor 29 reads out the second sequential B-mode image data Vy1 to VyM. The processor 29 detects one or more peak (or maximum) values Vmax of the volumes Vy1 to VyM and also one or more valley (or minimum) values Vmin of the volumes Vy1 to VyM. When the one or more peak (or maximum) values Vmax are detected, the processor 29 can recognize one or more B-mode image data which have the peak values Vmax. Accordingly, the processor 29 can determine the end-diastolic times, such as the first two-chamber end-diastolic time tx11' and the second two-chamber end-diastolic time tx12'.

Similarly, when the one or more valley (or minimum) values Vmin are detected, the processor 29 can recognize one or more B-mode image data which have the valley values Vmin. Accordingly, the processor can determine the end-systolic times, such as the first two-chamber end-systolic time tx21' and the second two-chamber end-systolic time tx22'. The determination of the first and second two-chamber end-diastolic times tx11', tx12' and the first and second two-chamber end-systolic times tx21', tx22' leads to determination of the first and second two-chamber systolic periods [tx11'–tx21'], [tx12'–tx22'] and the two-chamber diastolic period [tx21'–tx12']. Responsive to the determination of the periods, the processor 29 determines the number of the volume data (i.e., the number of the B-mode image data) included in each of the periods. This image number determination may substantially automatically be accomplished responsive to the period determination (step S16).

Based on the determination of the number of B-mode image data, the processor 29 advances to a time phase adjustment. The time phase adjustment will be made in the systolic periods between the first sequential B-mode image data and the second sequential B-mode image data. Further, the time phase adjustment will also be made in the diastolic periods between the first sequential B-mode image data and the second sequential B-mode image data. In the first embodiment of the present invention, a time phase of the second sequential B-mode image data is adjusted to a time phase of the first sequential B-mode image data. In other words, the time phase of the second sequential B-mode image data is adjusted based on the time phase of the first sequential B-mode image data.

Figure 9:
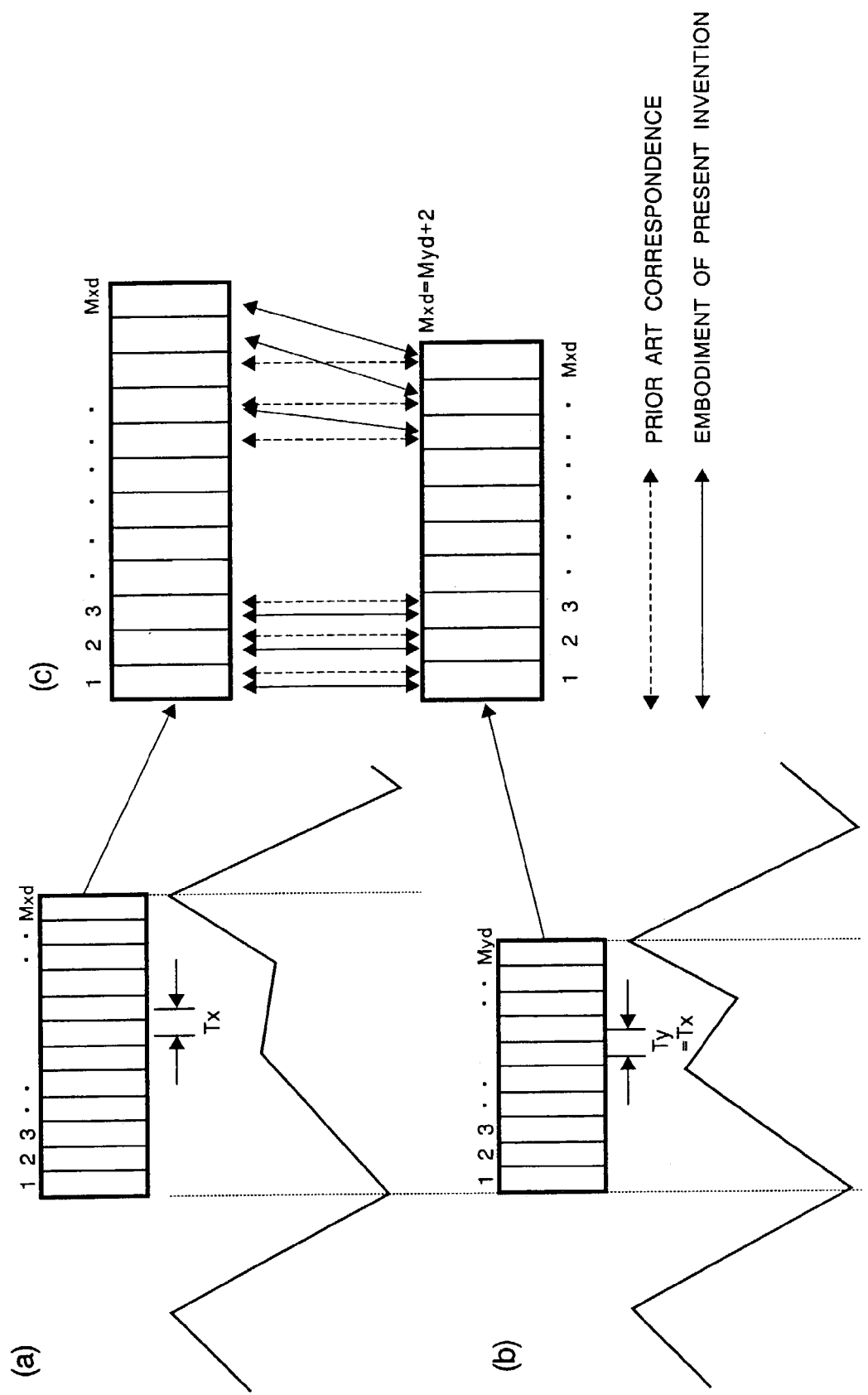
FIG. 9 is an illustration showing an example of a time phase adjustment between two kinds of sequential B-mode image data according to the first embodiment of the present invention.

FIG. 9 is an illustration showing an example of a time phase adjustment between two kinds of sequential B-mode image data according to the first embodiment of the present invention. FIG. 9(*a*) shows a relationship between the number of the first sequential B-mode image data belonging to the four-chamber diastolic period and a time-series volume transition chart of the first sequential B-mode image data. FIG. 9(*b*) shows a relationship between the number of the second sequential B-mode image data belonging to the two-chamber diastolic period and a time-series volume transition chart of the second sequential B-mode image data. Further, FIG. 9(*c*) shows an adjustment between a time phase of the first sequential B-mode image data belonging to the four-chamber diastolic period and a time phase of the second sequential B-mode image data belonging to the two-chamber diastolic period.

In general, the number of (B-mode) image data belonging to a diastolic period may be around 20 to 65, depending on the number of images acquired during one R-wave interval. The number of (B-mode) image data belonging to the diastolic period may become about two thirds of the number of images acquired during the one R-wave interval and may be more likely to be subject to the heart rate than that belonging to a systolic period.

The number of the B-mode image data belonging to the four-chamber diastolic period, (hereinafter referred to as the number of four-chamber diastole image data) may be herein defined as Mxd. Further, the number of the B-mode image data belonging to the first four-chamber systolic period, (hereinafter referred to as the number of four-chamber systole image data) may be herein defined as Mxs. Still further, an acquisition interval between each B-mode image data of the first sequential B-mode image data (hereinafter referred to as a first acquisition interval) may herein be defined as Tx. Similarly, regarding the second sequential B-mode image data, the number of the B-mode image data belonging to the two-chamber diastolic period, (hereinafter referred to as the number of two-chamber diastole image data) may be herein defined as Myd. Further, the number of the B-mode image data belonging to the first two-chamber systolic period, (hereinafter referred to as the number of two-chamber systole image data) may be herein defined as Mys. Still further, an acquisition interval between each B-mode image data of the second sequential B-mode image data (hereinafter referred to as a second acquisition interval) may herein be defined as Ty. Under conditions mentioned above, an adjustment coefficient Kd between the four-chamber and the two-chamber diastolic periods is represented with the following formula:

$$Kd = (Myd \times Ty)/(Mxd \times Tx) \qquad (7).$$

Similarly, an adjustment coefficient Ks between the first four-chamber and the first two-chamber systolic periods is represented with the following formula:

$$Ks = (Mys \times Ty)/(Mxs \times Tx) \qquad (8).$$

The first acquisition interval Tx, however, may usually be identical with the second acquisition interval Ty. Therefore, the formula (7) can be rewritten as the following formula (9):

$$Kd = Myd/Mxd \qquad (9).$$

Similarly, the formula (8) can be rewritten as the following formula (10):

$$Ks = Mys/Mxs \qquad (10).$$

As explained before, the number of four-chamber diastole image data Mxd and the number of four-chamber systole image data Mxs may easily (automatically) be obtained based on the time-series volume transition chart of the first sequential B-mode image data. Also, the number of two-chamber diastole image data Myd and the number of two-chamber systole image data Mys may easily (automatically) be obtained based on the time-series volume transition chart of the second sequential B-mode image data. On the other hand, the first acquisition interval Tx and the second acquisition interval Ty may be bound up with rate frequencies of and/or the number of scanning lines of the ultrasound diagnosis apparatus. Therefore, the first acquisition interval Tx and the second acquisition interval Ty are usually determined according to initialization of the ultrasound diagnosis apparatus.

In time phase adjusting two series of sequential image data according to an embodiment of the present invention, the correspondence between image data between the two series may depend upon a measured physical value that can differ between the two series. These physical values may be used, for example, to determine the adjustment coefficients, which are then used to determine which image in the first series corresponds to which image in the second series.

For example, when a $\beta d^{th}$ B-mode image data in the two-chamber diastolic period [tx21'–tx12'] (i.e., a specific frame or number of B-mode image data in the two-chamber diastolic period) may correspond, in time phase, to an $\alpha d^{th}$ B-mode image data in the four-chamber diastolic period [tx21–tx12] (i.e., a specific frame or number of B-mode image data in the four-chamber diastolic period), the $\beta d^{th}$ B-mode image data are calculated with the following formula (11):

$$\beta d = Kd \times \alpha d \qquad (11).$$

The α and β are only for distinguishing between four-chamber image data and two-chamber image data. The d is only for indicating image data in diastolic periods.

Thus, formulae (11) may be used to determine which frame or number of the more (less) numerous four-chamber image data in the diastolic period should appropriately correspond to a given frame or number of the less (more) numerous two-chamber image data in the diastolic period.

Similarly, when a $\beta s^{th}$ B-mode image data in the two-chamber systolic period [tx11'–tx21'] (i.e., a specific frame or number of B-mode image data in the two-chamber systolic period) may correspond, in time phase, to an $\alpha s^{th}$ B-mode image data in the four-chamber systolic period [tx11–tx21] (i.e., a specific frame or number of B-mode image data in the four-chamber systolic period), the $\beta s^{th}$ B-mode image data are calculated with the following formula (12):

$$\beta s = Ks \times \alpha s \qquad (12).$$

The s is only for indicating image data in systolic periods.

Thus, formulae (12) may be used to determine which frame or number of the more (less) numerous four-chamber image data in the systolic period should appropriately correspond to a given frame or number of the less (more) numerous two-chamber image data in the systolic period.

Such time phase adjustment calculations using the formulae (11) and (12), are also applied to all the B-mode image data of the first sequential B-mode image data, which belong to each of the four-chamber diastolic diastolic period [tx21–tx12] and the first four-chamber systolic period [tx11–tx21] (step S17). According to the time phase adjustment calculations, it may be quite rare that the βd obtained based on the formula (11) and/or the βs obtained based on the formula (12) become an integer. In practice, regarding the diastolic periods [tx21–tx12] and [tx21'–tx12'], two-chamber B-mode image data whose number is closest to the βd obtained based on the formula (11) may be used as the $\beta d^{th}$ two-chamber B-mode image data corresponding to the $\alpha d^{th}$ four-chamber B-mode image data. In the event, however, that a plurality of two-chamber B-mode image data happen to correspond to one four-chamber B-mode image data (alternatively, a plurality of four-chamber B-mode image data happen to correspond to one two-chamber B-mode image data) as a result of the use of image data closest to the calculated image number, a predetermined rule, regarding a principle of causality between the first sequential B-mode image data and the second sequential B-mode image data, may be determined in advance and the image correspondence may be determined in accordance with the predetermined rule. The predetermined rule may be, for example, (1) counting fractions 0.5 and over as one and disregarding the rest, (2) selecting, when a plurality of image data have decimals for one corresponding image data, one of the plurality of image data which has a closest (or nearest) decimal to an integer corresponding to an image number of the one corresponding image data, (3) selecting one image data acquired temporally closer to an acquisition time of one corresponding image data, and (4) any other rule, if necessary. Similarly, regarding the first systolic periods [tx11–tx21] and [tx11'–tx21'], two-chamber B-mode image data whose number is closest to the βs obtained based on the formula (12) may be used as the $\beta s^{th}$ two-chamber B-mode image data corresponding to the $\alpha s^{th}$ four-chamber B-mode image data. As mentioned above, in the event, however, that a plurality of two-chamber B-mode image data happen to correspond to one four-chamber B-mode image data (alternatively, a plurality of four-chamber B-mode image data happen to correspond to one two-chamber B-mode image data) as a result of the use of image data closest to the calculated image number, a predetermined rule, regarding a principle of causality between the first sequential B-mode image data and the second sequential B-mode image data, may be determined in advance and the image correspondence may be determined in accordance with the predetermined rule. The predetermined rule may be, for example, (1) counting fractions 0.5 and over as one and disregarding the rest, (2) selecting, when a plurality of image data have decimals for one corresponding image data, one of the plurality of image data which has a closest (or nearest) decimal to an integer corresponding to an image number of the one corresponding image data, (3) selecting one image data acquired temporally closer to an acquisition time of one corresponding image data, and (4) any other rule, if necessary.

As shown in FIG. 9(c), this is an exemplary case that the four-chamber diastolic period is about two Tx (time for acquiring two images) longer than the two-chamber diastolic period. In other words, the four-chamber diastolic period [tx21–tx12] includes two B-mode image data more than the two-chamber diastolic period [tx21'–tx12']. Therefore, a relationship between the number of four-chamber diastole image data Mxd and the number of two-chamber diastole image data Myd is represented by a formula Mxd=Myd+2. Accordingly, an $Myd^{th}$ two chamber diastole image data can correspond to an $(Myd+2)^{th}$ four-chamber diastole image data as a result of the time-phase adjustment. A time phase of B-mode image data at an edge of the two-chamber diastolic period [tx21'–tx12'] (or at the second two-chamber end-diastolic time tx12') can easily be adjusted with a time phase of B-mode image data at an edge of the four-chamber diastolic period [tx21–tx12] (or at the second four-chamber end-diastolic time tx12) in a manner mentioned above. However, B-mode image data other than the B-mode image data at edges of the periods may not be adjusted accurately in the above manner. For an accurate time phase adjustment, a use of the above explained formulae (11) and/or (12) may be advantageous, which makes it possible to adjust a time phase of the second sequential B-mode image data to a time phase of the first sequential B-mode image data when diastolic periods and/or systolic periods are different between the first and second sequential B-mode image data.

After the time phase adjustment in step S17, the processor 29 calculates a volume of the internal space of the heart chamber using time phase adjusted sequential B-mode image data (i.e., hypothetical sequential B-mode image data). The calculation is based on the already measured data regarding the first sequential B-mode image data and the second sequential B-mode image data. The diameter $A_j$ of the heart chamber in the $\alpha d^{th}$ B-mode image in the four-chamber diastolic period may be defined as A(αd)j. Regarding the first four-chamber systolic period, the diameter $A_j$ of the heart chamber in the $\alpha s^{th}$ B-mode image in the first four-chamber systolic period may be defined as A(αs)j. Similarly, the diameter Bj of the heart chamber in the $\beta d^{th}$ B-mode image in the two-chamber diastolic period may be defined as B(βd)j. Regarding the first two-chamber systolic period, the diameter Bj of the heart chamber in the $\beta s^{th}$ B-mode image in the first two-chamber systolic period may be defined as B(βs)j. Although the volume of the internal space of the heart chamber in the four-chamber (or the two-chamber) B-mode image data has been calculated with the formula (1) (or (4)), the formula (1) (or (4)) may be modified and replaced with a formula (13) (or (15)) shown below when such a calculation is applied to a volume calculation of the internal space of the heart chamber in the time-phase adjusted B-mode image data.

A volume $V(\alpha d)$ of the time-phase adjusted B-mode image data corresponding to an $\alpha d^{th}$ four-chamber B-mode image data in the four-chamber diastolic period may be calculated with the following formula (13):

$$V(\alpha d)=\Sigma \Delta h \times \pi (A(\alpha d)j/2)(B(\beta d)j/2) \ (j=1 \ to \ J) \quad (13).$$

According to the formula (11), $\beta d = Kd \times \alpha d$. Therefore, the formula (13) is rewritten as follows:

$$V(\alpha d)=(\pi h/4)\Sigma(A(\alpha d)j)(B(Kd \cdot \alpha d)j) \ (j=1 \ to \ J) \quad (14)$$

As described before, the coefficient Kd is available according to the formula (7) or (9). In this case, the diameters $A(\alpha d)j$ and $B(Kd \cdot \alpha d)j$ may be expressed as follows:

$$A(\alpha d)j=(a(\alpha d)_{j-1}+a(\alpha d)_j)/2$$

$$B(Kd \cdot \alpha d)j=(b(Kd \cdot \alpha d)_{j-1}+b(Kd \cdot \alpha d)_j)/2$$

When it comes to the first systolic periods, a volume $V(\alpha s)$ of the time-phase adjusted B-mode image data corresponding to an $\alpha s^{th}$ four-chamber B-mode image data in the first four-chamber systolic period may be calculated with the following formula (15):

$$V(\alpha s)=\Sigma \Delta h \times \pi (A(\alpha s)j/2)(B(\beta s)j/2) \ (j=1 \ to \ J) \quad (15)$$

According to the formula (12), $\beta s = Ks \times \alpha s$. Therefore, the formula (15) is rewritten as follows:

$$V(\alpha s)=(\pi h/4)\Sigma(A(\alpha s)j)(B(Ks \cdot \alpha s)j) \ (j=1 \ to \ J) \quad (16)$$

As described before, the coefficient Ks is available according to the formula (8) or (10). In this case, the diameters $A(\alpha s)j$ and $B(Ks \cdot \alpha s)j$ may be expressed as follows:

$$A(\alpha s)j=(a(\alpha s)_{j-1}+a(\alpha s)_j)/2$$

$$B(Ks \cdot \alpha s)j=(b(Ks \cdot \alpha s)_{j-1}+b(Ks \cdot \alpha s)_j)/2$$

In accordance with the above formulae (14) and (16), one can obtain the volume, regarding the each period, of the internal space of the heart chamber in the time-phase adjusted B-mode image data (step S18).

Figure 10:
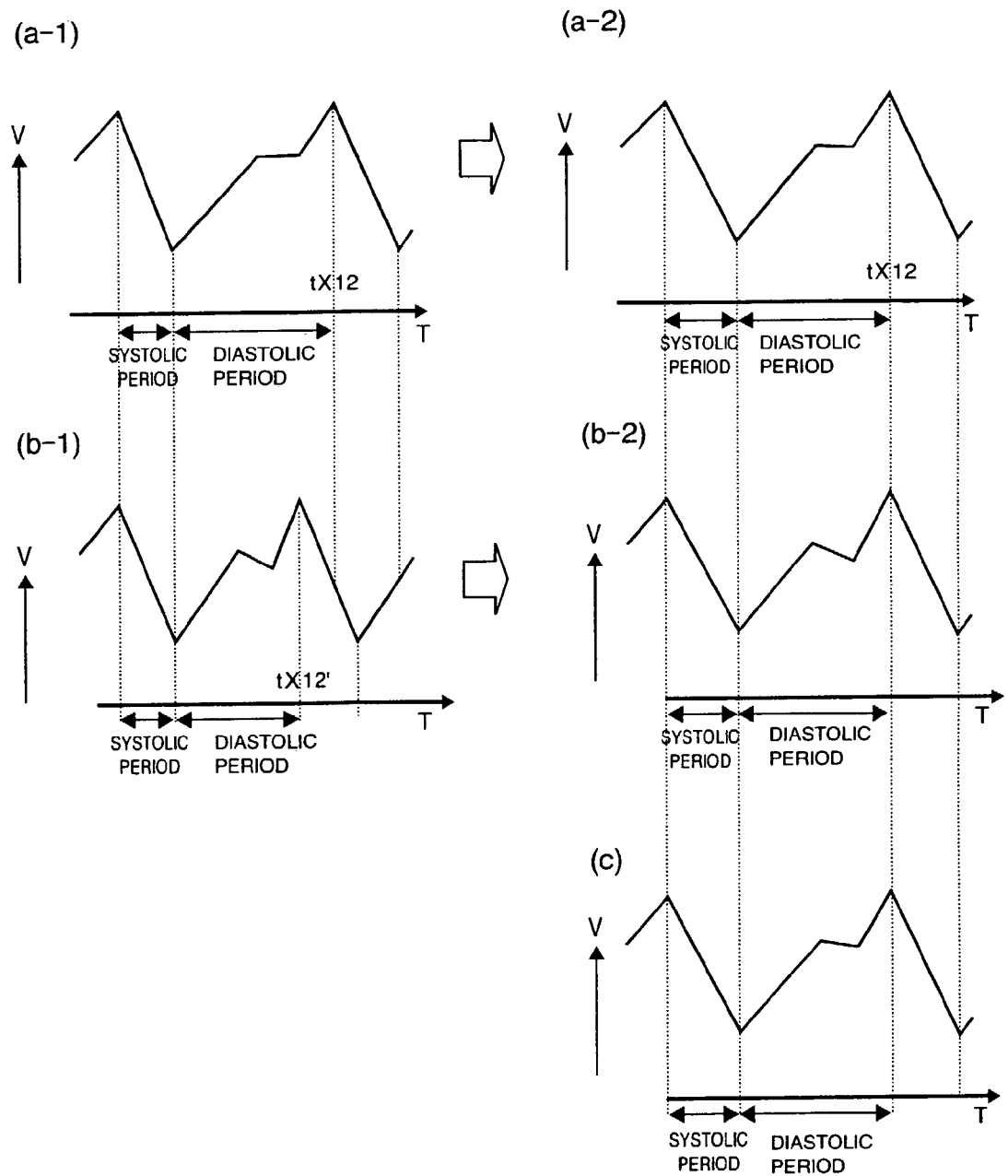
FIG. 10 is an illustration showing time-series volume transitions before and after the time phase adjustment according to the first embodiment of the present invention.

For reference data for explaining advantages resulting from the time phase adjustment according to the first embodiment of the present invention, charts of respective time-series volume transitions of the first and second sequential B-mode image data before and after the time-phase adjustment will be described with reference to FIG. 10. FIG. 10 is an illustration showing time-series volume transitions before and after the time phase adjustment according to the first embodiment of the present invention. To be more in detail, FIG. 10(a-1) shows an example of a time-series volume transition of the first sequential B-mode image data before the time phase adjustment. In addition, FIG. 10(a-2) shows an example of a time-series volume transition of the first sequential B-mode image data after the time phase adjustment. Similarly, FIG. 10(b-1) shows an example of a time-series volume transition of the second sequential B-mode image data before the time phase adjustment. In addition, FIG. 10(b-2) shows an example of a time-series volume transition of the second sequential B-mode image data after the time phase adjustment. Still further, FIG. 10(c) shows an example of a time-series volume transition of the sequential B-mode image data obtained based on the formulae (14) and (16).

Compared to the first sequential B-mode image data in the four-chamber diastolic period, the second sequential B-mode image data in the two-chamber diastolic period have less images due to a time phase shift. As shown in FIG. 10, the second four-chamber end-diastolic time tx12 in FIG. 10(a-1) is not in time phase with the second two-chamber end-diastolic time tx12' in FIG. 10(b-1). As a result of the time phase adjustment described above, the time phase difference between the first and second sequential B-mode image data is corrected so as to adjust the second two-chamber end-diastolic time tx12' to match the second four-chamber end-diastolic time tx12 as shown in FIGS. 10(a-2),(b-2). Accordingly, the volume calculations described with the formulae (14) and (16) will be performed on the hypothetical sequential B-mode image data. A time-series volume transition of the hypothetical sequential B-mode image data may be represented as a chart shown in FIG. 10(c).

According to the first embodiment of the present invention, when the processor 29 calculates volume transitions of the internal space of the heart chamber applying the Modified-Simpson technique to the first and second sequential B-mode image data, the processor 29 detects the respective time phases from the time-series volume transitions obtained based on the first and second sequential B-mode image data. Further, the processor 29 adjusts the time phase between the first and second sequential B-mode image data in accordance with the detected result. Therefore, the first and second sequential B-mode image data are adjusted so that their time-phases are substantially identical in advance of the application of the Modified-Simpson technique. This may make it possible to perform an accurate volume measurement, compared to the prior art measurement.

(Second Embodiment)

Next, a second embodiment of the present invention will be described with reference to FIGS. 2, and 10 to 14. In the first embodiment of the present invention, it has been described to improve measurement accuracies, adjusting a time phase between two kinds of sequential B-mode image data, when various measurements are performed on the two kinds of sequential B-mode image data obtained under two different conditions, respectively. According to the second embodiment of the present invention, however, it will be described to adjust a time phase between the two kinds of sequential B-mode image data obtained under two different conditions and to display two kinds of sequential images in time phase side by side (or in parallel). The two kinds of sequential images to be displayed may be two kinds of sequential images resulting from the synthesis between the two kinds of sequential B-mode image data and two kinds of sequential Doppler-mode image data corresponding to the two kinds of sequential B-mode image data. Alternatively, the two kinds of sequential images to be displayed may be two kinds of sequential B-mode images based on the two kinds of sequential B-mode image data. Still alternatively, the two kinds of sequential images to be displayed may be two kinds of sequential Doppler-mode images corresponding to the two kinds of sequential B-mode image data.

In the following description, the second embodiment of the present invention will be described taking an example of a case that first sequential images showing the four-chamber view and second sequential images showing the two-chamber view are simultaneously displayed. Procedures for an image data acquisition according to the second embodiment of the present invention may be similar to those in FIG. 3 described according to the first embodiment of the present invention. Therefore, the procedures for the image data acquisition will be omitted below.

Figure 11:
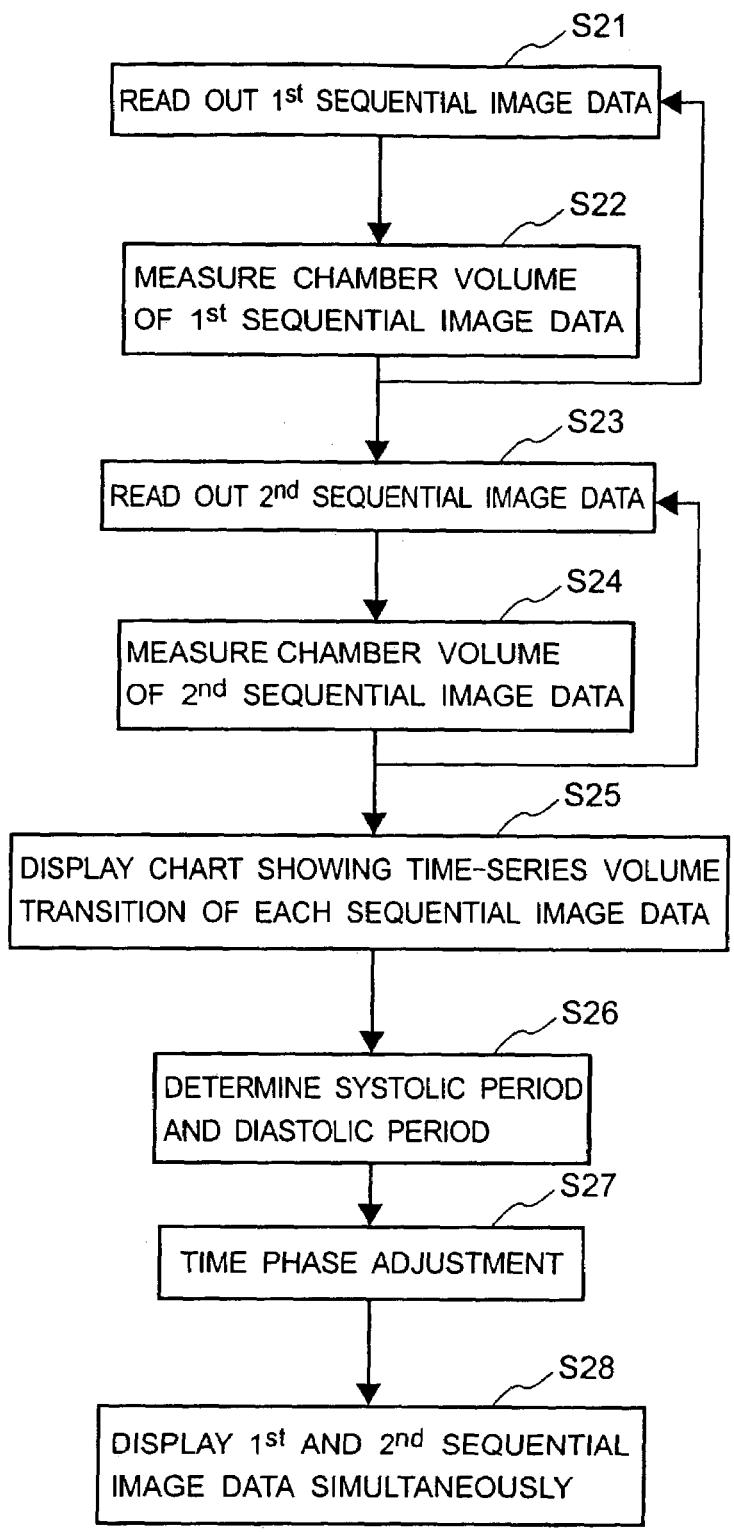
FIG. 11 is a flowchart showing an example of procedures for a simultaneous display based on the time phase adjustment according to a second embodiment of the present invention.

FIG. 11 is a flowchart showing an example of procedures for a simultaneous display based on the time phase adjustment according to the second embodiment of the present invention. The processor 29 reads out first B-mode image data Ix1 of the four-chamber view from the first sequential B-mode image data (Ix1 to IxM) stored in the memory 28 (step S21). The processor 29 uses a contour extraction technique to extract a heart chamber (e.g., a left ventricle) lining in the first B-mode image data Ix1. For example, the heart chamber lining may be extracted by the processor 29, using the ACT method. The processor 29 extracts a contour of the heart chamber lining in accordance with the ACT method and accordingly detects a mitral annulus from the extracted contour. Further, the processor 29 determines a long axis in the longitudinal direction of the heart chamber based on the mitral annulus. When a height of the heart chamber lining along the long axis is h, for example, a length of the long axis is also h. The long axis may be divided, at predetermined points hj (j=1 to J), into a predetermined number J (e.g., J=20) of line segments each of which has a same length $\Delta h$ ($\Delta h = h/J$). In this case, it may be possible to treat an internal space of the heart chamber as a gathering of the predetermined number J of blocks each of which has a same height $\Delta h$ along the long axis. When a line that is perpendicular to the long axis at a predetermined point hj is drawn to the heart chamber lining, the perpendicular line intersects with the heart chamber lining at given two points. The processor 29 may calculate a length $A_j$ of the perpendicular line between the two points. The length h, the length $A_j$, and any other related data mentioned above, if necessary, are stored in the auxiliary memory of the memory 28. One block j of the J blocks under the above condition may be assumed to be a column comprising the height $\Delta h$ and a circular surface with a diameter $A_j$. Accordingly, a volume $V_{Aj}$ of the block j can be approximated by a formula: $V_{Aj} = \Delta h \times \pi (A_j/2)^2$. In this assumption, according to the Modified-Simpson technique, a volume Vx1 of the internal space can be approximated to a result of summing the volume $V_{Aj}$ on all the J blocks (Vx1 = $V_{A1} + V_{A2} + \ldots + V_{AJ}$). This is represented with the following formula: Vx1 = $\Sigma \Delta h \times \pi (A_j/2)^2$ (j=1 to J). In order to obtain a more correct volume of the internal space, the diameter $A_j$ described above may be calculated as follows.

The one block j of the J blocks may usually not be a complete column. In other words, the one block j may have a lower surface assumed to be a circle with a diameter $a_j$ (j=1 to J) and an upper surface with a diameter $a_{j-1}$. When 'j' represents an odd number, the diameter $a_j$ is a diameter of a surface which comes in an odd-numbered order while the diameter $a_{j-1}$ is a diameter of a surface which comes in an even-numbered order. Similarly, when 'j' represents an even number, the diameter $a_j$ is a diameter of a surface which comes in an even-numbered order while the diameter $a_{j-1}$ is a diameter of a surface which comes in an odd-numbered order. As described above, the height of the one block may be defined as $\Delta h$ ($\Delta h = h/J$). Therefore, if one takes a diameter ($A_j$) at the height $\Delta h/2$ of the one block j as each of an approximated diameter of the lower surface and an approximated diameter of the upper surface, the diameter $A_j$ may be represented as $(a_{j-1} + a_j)/2$. This means that the one block j can be assumed to be a column, which comprises the height $\Delta h$ and a circular surface with a diameter $A_j$ ($A_j = (a_{j-1} + a_j)/2$). Therefore, the formula of the volume Vx1 can be replaced with the following formula: Vx1 = $\Sigma \Delta h \times \pi (((a_{j-1} + a_j)/2)/2)^2$ (j=1 to J). Since the height $\Delta h$ has been defined as $\Delta h = h/J$, the volume Vx1 can be further rewritten as the following formula: Vx1 = $(\pi h/16) \Sigma (a_{j-1} + a_j)^2$ (j=1 to J) ... (17). The processor 29 sends the volume Vx1 calculated in the above calculation to the memory 28. In the memory 28, the volume Vx1 is stored in the auxiliary memory (step S22).

After the volume calculation (or measurement) for the first B-mode image data Ix1 of the four-chamber view included in the first sequential B-mode image data (Ix1 to IxM), the second B-mode image data Ix2 is read out from the memory 28 by the processor 29. Again, the processor 29 uses a contour extraction technique to extract a heart chamber lining in the second B-mode image data Ix2. The heart chamber for its lining extraction in the second B-mode image data Ix2 is the same as that in the first B-mode image data Ix1. A volume Vx2 of an internal space of the heart chamber is obtained in a manner similar to the calculation of the volume Vx1 in the first B-mode image data Ix1. Repeating similar procedures, the processor 29 obtains volumes Vx3 to VxM for the third to the $M^{th}$ B-mode image data. The volumes Vx2 to VxM are stored in the auxiliary memory of the memory 28, respectively, as each of the volumes Vx2 to VxM is obtained (steps S21 to S22).

The processor 29 then reads out first B-mode image data Iy1 of the two-chamber view from the second sequential B-mode image data (Iy1 to IyM) stored in the memory 28 (step S23). The processor 29 uses a contour extraction technique to extract a heart chamber lining in the first B-mode image data Iy1. The heart chamber for its lining extraction in the second sequential B-mode image data (Iy1 to IyM) is the same as that in the first sequential B-mode image data (Ix1 to IxM).

For example, the heart chamber lining may be extracted by the processor 29, using the ACT method. As described for the first sequential B-mode image data (Ix1 to IxM), the processor 29 extracts a contour of the heart chamber lining in accordance with the ACT method and accordingly detects a mitral annulus from the extracted contour. Further, the processor 29 determines a long axis in the longitudinal direction of the heart chamber based on the mitral annulus. When a height of the heart chamber lining along the long axis is h, for example, a length of the long axis is also h. The long axis may be divided, at predetermined points hj (j=1 to J), into the predetermined number J of line segments each of which has a same length $\Delta h$ ($\Delta h = h/J$). In this case, it may also be possible to treat an internal space of the heart chamber as a gathering of the predetermined number J of blocks each of which has a same height $\Delta h$ along the long axis. When a line that is perpendicular to the long axis at a predetermined point hj is drawn to the heart chamber lining, the perpendicular line intersects with the heart chamber lining at two points. The processor 29 may calculate a length Bj of the perpendicular line between the two points. The length h, the length Bj, and any other related data mentioned above, if necessary, are stored in the auxiliary memory of the memory 28. One block j of the J blocks under the above condition may be assumed to be a column comprising the height $\Delta h$ and a circular surface with a diameter Bj. Accordingly, a volume $V_{Bj}$ of the block j can be approximated by a formula: $V_{Bj} = \Delta h \times \pi (Bj/2)^2$ In this assumption, according to the Modified-Simpson technique, a volume Vy1 of the internal space can be approximated to a result of summing the volume $V_{Bj}$ on all the J blocks (Vy1 = $V_{B1} + V_{B2} + \ldots + V_{BJ}$). This is represented with the following formula: Vy1 = $\Sigma \Delta h \times \pi (Bj/2)^2$ (j=1 to J). As similar to the first sequential B-mode image data, in order to obtain a more correct volume of the internal space, the diameter Bj described above may be calculated as follows.

The one block j of the J blocks may usually not be a complete column. In other words, the one block j may have a lower surface assumed to be a circle with a diameter $b_j$ (j=1 to J) and an upper surface with a diameter $b_{j-1}$. When 'j' represents an odd number, the diameter $b_j$ is a diameter of a surface which comes in an odd-numbered order while the diameter $b_{j-1}$ is a diameter of a surface which comes in an even-numbered order. Similarly, when 'j' represents an even number, the diameter $b_j$ is a diameter of a surface which comes in an even-numbered order while the diameter $b_{j-1}$ is a diameter of a surface which comes in an odd-numbered order. As described above, the height of the one block may be defined as $\Delta h$ ($\Delta h = h/J$). Therefore, if one takes a diameter (Bj) at the height $\Delta h/2$ of the one block j as each of an approximated diameter of the lower surface and an approximated diameter of the upper surface, the diameter Bj may be represented as $(b_{j-1}+b_j)/2$. This means that the one block j can be assumed to be a column, which comprises the height $\Delta h$ and a circular surface with a diameter Bj (Bj=$(b_{j-1}+b_j)/2$). Therefore, the formula of the volume Vy1 can be replaced with the following formula: Vy1=$\Sigma \Delta h \times \pi(((b^{j-1}+b_j)/2)/2)^2$ (j=1 to J). Since the height $\Delta h$ has been defined as $\Delta h = h/J$, the volume Vy1 can be further rewritten as the following formula: Vy1=$(\pi h/16)\Sigma(b_{j-1}+b_j)^2$ (j=1 to J) . . . (18). The processor 29 sends the volume Vy1 calculated in the above calculation to the memory 28. In the memory 28, the volume Vy1 is stored in the auxiliary memory (step S24).

After the volume calculation (or measurement) for the first B-mode image data Iy1 of the two-chamber view included in the second sequential B-mode image data (Iy1 to IyM), the second B-mode image data Iy2 is read out from the memory 28 by the processor 29. Again, the processor 29 uses a contour extraction technique to extract a heart chamber lining in the second B-mode image data Iy2. The heart chamber for its lining extraction in the second B-mode image data Iy2 is the same as that in the first B-mode image data Iy1. A volume Vy2 of an internal space of the heart chamber is obtained in a manner similar to the calculation of the volume Vy1 in the first B-mode image data Iy1. Repeating similar procedures, the processor 29 obtains volumes Vy3 to VyM for the third to the M$^{th}$ B-mode image data. The volumes Vy2 to VyM are stored in the auxiliary memory of the memory 28, respectively, as each of the volumes Vy2 to VyM is obtained (steps S23 to S24).

After obtaining both the volumes (or volume data) Vx1 to VxM in the four-chamber view and Vy1 to VyM in the two-chamber view, the system control unit 9 controls to temporarily store the volumes Vx1 to VxM and Vy1 to VyM in the display memory 30. The stored volumes Vx1 to VxM and Vy1 to VyM are then displayed in the monitor 32 through the display circuit 31 in a form of a time-series volume transition (step S25).

In a time-series volume transition chart, volumes calculated by applying the formula (17) to each B-mode image data of the first sequential B-mode image data are plotted in time-series along acquisition of the first sequential B-mode image data. Similarly, in the time-series volume transition chart, volumes calculated by applying the formula (18) to each B-mode image data of the second sequential B-mode image data are plotted in time-series along acquisition of the second sequential B-mode image data. The each B-mode image data of the first sequential B-mode image data may be acquired at an interval Tx. The each B-mode image data of the second sequential B-mode image data may be acquired at an interval Ty.

In the time-series volume transition chart of four-chamber view image data, a first peak at a time phase tx11 may be determined to be a first four-chamber end-diastolic time. The first peak is a time when the calculated volume Vx becomes greatest for the first time among the first sequential B-mode image data. Also a second peak at a time phase tx12 may be determined to be a second four-chamber end-diastolic time. The second peak is a time when the calculated volume Vx becomes greatest for the second time among the first sequential B-mode image data. On the other hand, a first valley at a time phase tx21 may be determined to be a first four-chamber end-systolic time. The first valley is a time when the calculated volume Vx becomes smallest for the first time among the first sequential B-mode image data. Also a second valley at a time phase tx22 may be determined to be a second four-chamber end-systolic time. The second valley is a time when the calculated volume Vx becomes smallest for the second time among the first sequential B-mode image data. A period between the first four-chamber end-diastolic time tx11 and the first four-chamber end-systolic time tx21 is determined to be a first four-chamber systolic period [tx11–tx21]. A period between the second four-chamber end-diastolic time tx12 and the second four-chamber end-systolic time tx22 is determined to be a second four-chamber systolic period [tx12–tx22]. In addition, a period between the first four-chamber end-systolic time tx21 and the second four-chamber end-diastolic time tx12 is determined to be a four-chamber diastolic period [tx21–tx12].

In the time-series volume transition chart of two-chamber view image data, a first peak at a time phase tx11' may be determined to be a first two-chamber end-diastolic time. The first peak is a time when the calculated volume Vy becomes greatest for the first time among the second sequential B-mode image data. Also a second peak at a time phase tx12' may be determined to be a second two-chamber end-diastolic time. The second peak is a time when the calculated volume Vy becomes greatest for the second time among the second sequential B-mode image data. On the other hand, a first valley at a time phase tx21' may be determined to be a first two-chamber end-systolic time. The first valley is a time when the calculated volume Vy becomes smallest for the first time among the second sequential B-mode image data. Also a second valley at a time phase tx22' may be determined to be a second two-chamber end-systolic time. The second valley is a time when the calculated volume Vy becomes smallest for the second time among the second sequential B-mode image data. A period between the first two-chamber end-diastolic time tx11' and the first two-chamber end-systolic time tx21' is determined to be a first two-chamber systolic period [tx11'–tx21']. A period between the second two-chamber end-diastolic time tx12' and the second two-chamber end-systolic time tx22' is determined to be a second two-chamber systolic period [tx12'–tx22']. In addition, a period between the first two-chamber end-systolic time tx21' and the second two-chamber end-diastolic time tx12' is determined to be a two-chamber diastolic period [tx21'–tx12'].

In order to determine the times and the periods of the first sequential B-mode image data described above, the processor 29 reads out the first sequential B-mode image data Vx1 to VxM. The processor 29 detects one or more peak (or maximum) values Vmax of the volumes Vx1 to VxM and also one or more valley (or minimum) values Vmin of the volumes Vx1 to VxM. When the one or more peak (or maximum) values Vmax are detected, the processor 29 can recognize one or more B-mode image data which have the peak values Vmax. Accordingly, the processor 29 can determine the end-diastolic times, such as the first four-chamber end-diastolic time tx11 and the second four-chamber end-diastolic time tx12. Similarly, when the one or more valley (or minimum) values Vmin are detected, the processor 29 can recognize one or more B-mode image data which have the valley values Vmin. Accordingly, the processor can determine the end-systolic times, such as the first four-chamber end-systolic time tx21 and the second four-chamber end-systolic time tx22. The determination of the first and second four-chamber end-diastolic times tx11, tx12 and the first and second four-chamber end-systolic times tx21, tx22 leads to determination of the first and second four-chamber systolic periods [tx11–tx21], [tx12–tx22] and the four-chamber diastolic period [tx21–tx12]. Responsive to the determination of the periods, the processor 29 determines the number of the volume data (i.e., the number of the B-mode image data) included in each of the periods. This image number determination may substantially automatically be accomplished responsive to the period determination.

Similarly, in order to determine the times and the periods of the second sequential B-mode image data described above, the processor 29 reads out the second sequential B-mode image data Vy1 to VyM. The processor 29 detects one or more peak (or maximum) values Vmax of the volumes Vy1 to VyM and also one or more valley (or minimum) values Vmin of the volumes Vy1 to VyM. When the one or more peak (or maximum) values Vmax are detected, the processor 29 can recognize one or more B-mode image data which have the peak values Vmax. Accordingly, the processor 29 can determine the end-diastolic times, such as the first two-chamber end-diastolic time tx11' and the second two-chamber end-diastolic time tx12'. Similarly, when the one or more valley (or minimum) values Vmin are detected, the processor 29 can recognize one or more B-mode image data which have the valley values Vmin. Accordingly, the processor can determine the end-systolic times, such as the first two-chamber end-systolic time tx21' and the second two-chamber end-systolic time tx22'. The determination of the first and second two-chamber end-diastolic times tx11', tx12' and the first and second two-chamber end-systolic times tx21', tx22' leads to determination of the first and second two-chamber systolic periods [tx11'–tx21'], [tx12'–tx22'] and the two-chamber diastolic period [tx21'–tx12']. Responsive to the determination of the periods, the processor 29 determines the number of the volume data (i.e., the number of the B-mode image data) included in each of the periods. This image number determination may substantially automatically be accomplished responsive to the period determination (step S26).

Based on the determination of the number of B-mode image data, the processor 29 advances to a time phase adjustment. The time phase adjustment will be made in the systolic periods between the first sequential B-mode image data and the second sequential B-mode image data. Further, the time phase adjustment will also be made in the diastolic periods between the first sequential B-mode image data and the second sequential B-mode image data. In the first embodiment of the present invention, a time phase of the second sequential B-mode image data is adjusted to a time phase of the first sequential B-mode image data. In other words, the phase of the second sequential B-mode image data is adjusted based on the time phase of the first sequential B-mode image data.

The number of four-chamber diastole image data may be herein defined as Mxd. Further, the number of four-chamber systole image data may be herein defined as Mxs. Still further, the first acquisition interval may herein be defined as Tx. Similarly, regarding the second sequential B-mode image data, the number of two-chamber diastole image data may be herein defined as Myd. Further, the number of two-chamber systole image data may be herein defined as Mys. Still further, the second acquisition interval may herein be defined as Ty. Under conditions mentioned above, an adjustment coefficient Kd between the four-chamber and the two-chamber diastolic periods is represented with the following formula: Kd=(Myd×Ty)/(Mxd×Tx). Similarly, an adjustment coefficient Ks between the first four-chamber and the first two-chamber systolic periods is represented with the following formula: Ks=(Mys×Ty)/(Mxs×Tx). The first acquisition interval Tx, however, may usually be identical with the second acquisition interval Ty. Therefore, the formula of the coefficient Kd can be rewritten as the following formula: Kd=Myd/Mxd. Similarly, the formula of the coefficient Ks can be rewritten as the following formula: Ks=Mys/Mxs.

As explained before, the number of four-chamber diastole image data Mxd and the number of four-chamber systole image data Mxs may easily (automatically) be obtained based on the time-series volume transition chart of the first sequential B-mode image data. Also, the number of two-chamber diastole image data Myd and the number of two-chamber systole image data Mys may easily (automatically) be obtained based on the time-series volume transition chart of the second sequential B-mode image data. On the other hand, the first acquisition interval Tx and the second acquisition interval Ty may be bound up with rate frequencies of and/or the number of scanning lines of the ultrasound diagnosis apparatus. Therefore, the first acquisition interval Tx and the second acquisition interval Ty are usually determined according to initialization of the ultrasound diagnosis apparatus.

For example, when a $\beta d^{th}$ B-mode image data in the two-chamber diastolic period [tx21'–tx12'] (i,.e., a $\beta d^{th}$ B-mode image data from the first two-chamber end-systolic time tx21') may correspond, in time phase, to an $\alpha d^{th}$ B-mode image data in the four-chamber diastolic period [tx21–tx12] (i.e., an $\alpha d^{th}$ B-mode image data from the first four-chamber end-systolic time tx21), the $\beta d^{th}$ B-mode image data are calculated with the following formula: $\beta d = Kd \times \alpha d$. Similarly, when a $\beta s^{th}$ B-mode image data in the two-chamber systolic period [tx11'–tx21'] (i.e., a $\beta s^{th}$ B-mode image data from the first two-chamber end-diastolic time tx11') may correspond, in time phase, to an $\alpha s^{th}$ B-mode image data in the four-chamber systolic period [tx11–tx21] (i.e., an $\alpha s^{th}$ B-mode image data from the first four-chamber end-diastolic time tx11), the $\beta s^{th}$ B-mode image data are calculated with the following formula: $\beta s = Ks \times \alpha s$.

Such time phase adjustment calculations are also applied to all the B-mode image data of the first sequential B-mode image data, which belong to each of the four-chamber diastolic diastolic period [tx21–tx12] and the first four-chamber systolic period [tx11–tx21] (step S27). According to the time phase adjustment calculations, it may be quite rare that the βd and/or the βs become an integer. In practice, regarding the diastolic periods [tx21–tx12] and [tx21'–tx12'], two-chamber B-mode image data whose number is closest to the βd may be used as the $\beta d^{th}$ two-chamber B-mode image data corresponding to the $\alpha d^{th}$ four-chamber B-mode image data. In the event, however, that a plurality of two-chamber B-mode image data happen to correspond to one four-chamber B-mode image data (alternatively, a plurality of four-chamber B-mode image data happen to correspond to one two-chamber B-mode image data) as a result of the use of image data closest to the calculated image number, a predetermined rule, regarding a principle of causality between the first sequential B-mode image data and the second sequential B-mode image data, may be determined in advance and the image correspondence may be determined in accordance with the predetermined rule. The predetermined rule may be, for example, (1) counting fractions 0.5 and over as one and disregarding the rest, (2) selecting, when a plurality of image data have decimals for one corresponding image data, one of the plurality of image data which has a closest (or nearest) decimal to an integer corresponding to an image number of the one corresponding image data, (3) selecting one image data acquired temporally closer to an acquisition time of one corresponding image data, and (4) any other rule, if necessary. Similarly, regarding the first systolic periods [tx11–tx21] and [tx11'–tx21'], two-chamber B-mode image data whose number is closest to the $\beta s$ may be used as the $\beta s^{th}$ two-chamber B-mode image data corresponding to the $\alpha s^{th}$ four-chamber B-mode image data. As mentioned above, in the event, however, that a plurality of two-chamber B-mode image data happen to correspond to one four-chamber B-mode image data (alternatively, a plurality of four-chamber B-mode image data happen to correspond to one two-chamber B-mode image data) as a result of the use of image data closest to the calculated image number, a predetermined rule, regarding a principle of causality between the first sequential B-mode image data and the second sequential B-mode image data, may be determined in advance and the image correspondence may be determined in accordance with the predetermined rule. The predetermined rule may be, for example, (1) counting fractions 0.5 and over as one and disregarding the rest, (2) selecting, when a plurality of image data have decimals for one corresponding image data, one of the plurality of image data which has a closest (or nearest) decimal to an integer corresponding to an image number of the one corresponding image data, (3) selecting one image data acquired temporally closer to an acquisition time of one corresponding image data, and (4) any other rule, if necessary.

According to the procedures described above, even when respective diastolic periods and/or respective systolic periods are different in their lengths between the first and the second sequential image data, the processor 29 makes calculations on the first and the second sequential image data, using the coefficients Kd and Ks for correcting a time phase difference, so as to adjust time phases between the first and the second sequential image data. Accordingly, it can be possible to obtain one predetermined image data included in the first (or the second) sequential image data which corresponds to another predetermined image data included in the second (or the first) sequential image data. A time phase of the one predetermined image data included in the first (or the second) sequential image data may be substantially identical with a time phase of the another predetermined image data included in the second (or the first) sequential image data.

Figure 12:
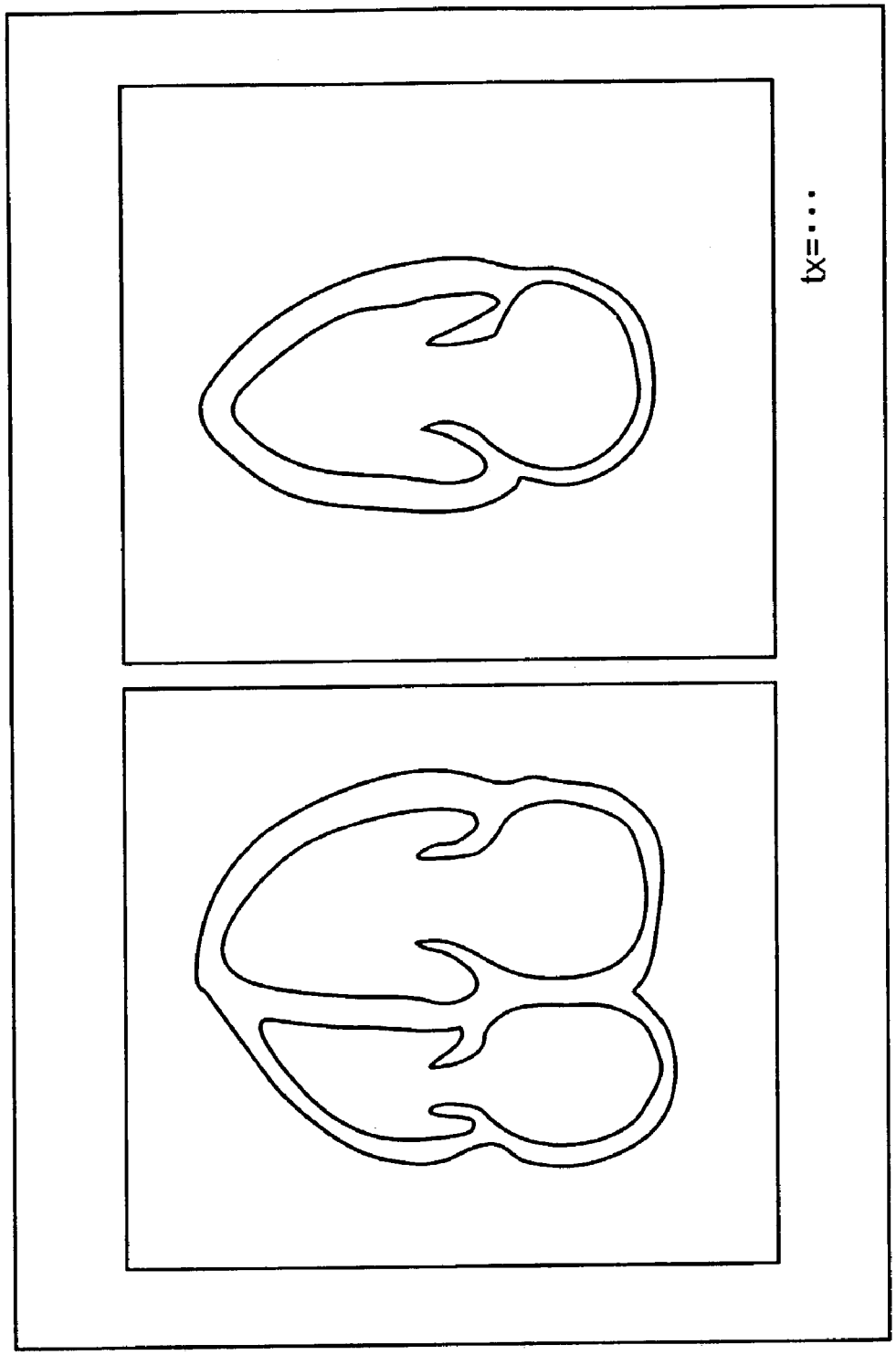
FIG. 12 is an illustration showing an example of a parallel display of the time-phase adjusted first and second sequential image according to the second embodiment of the present invention.

After the time phase adjustment, the system control unit 9 reads out the first sequential image data and the second sequential image data from the memory 28. The read-out first and second sequential image data are converted from their formats into formats for a parallel display in the display memory 30. The display memory 30 stores the format-converted first and second sequential image data. The stored first and second sequential image data are sent to the monitor 32 through the display circuit 31. In the monitor 32, the first and second sequential images are displayed in parallel in a time-phase adjusted manner, as shown in FIG. 12 (step S28).

The parallel display may be made by, but not limited to, displaying the first and second sequential images side by side. The parallel display may also be interpreted as a simultaneous display of the first and second sequential images. In FIG. 12, the first sequential images representing the four-chamber view of the heart may be displayed in the left side of the monitor 32. In the right side of the monitor 32, the second sequential images representing the two-chamber view of the heart may be displayed. And vice versa. Further, the first and second sequential images may be displayed one above the other as a kind of parallel or simultaneous display. Still further, when there are provided two monitors as the monitor 32 which are operative under a single CPU (central processing unit), the first sequential images may be displayed in a first of the two monitors. The second sequential images may be displayed in a second of the two monitors in time phase with the first sequential images displayed in the first monitor. The first and second sequential images may be displayed in conjunction with each other in the time-phase adjusted manner under controls of the single CPU. Such two-monitor display may also be included in the parallel display.

Figures 13, 14:
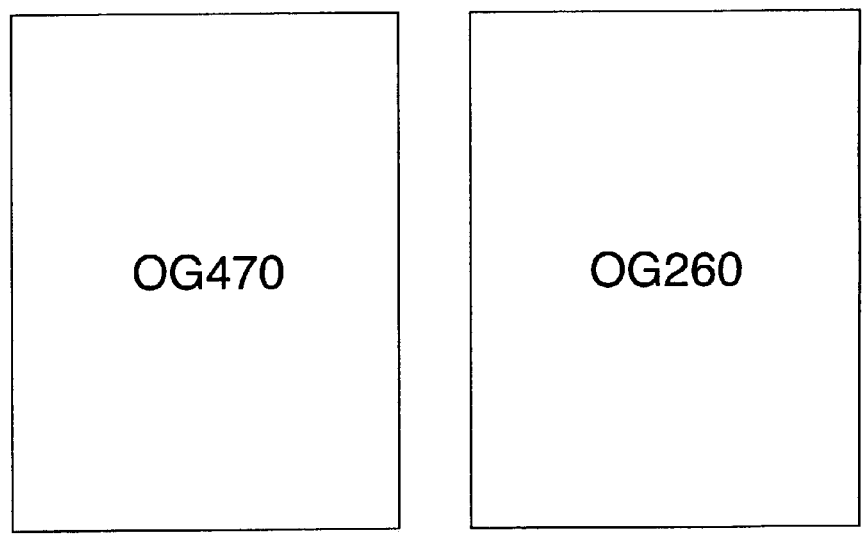
FIG. 13 is an illustration showing an example of thumbnails, displayed in parallel, of the time-phase adjusted first and second sequential images according to the second embodiment of the present invention.
FIG. 14 is an illustration showing an example of a parallel display after a thumbnails display according to the second embodiment of the present invention.

FIG. 13 is an illustration showing an example of thumbnails, displayed in parallel, of the time-phase adjusted first and second sequential images according to the second embodiment of the present invention. In FIG. 13, instead of the first sequential images, four-chamber view images are displayed in thumbnails 410 to 490. In addition, two-chamber view images are displayed in thumbnails 210 to 270 instead of the second sequential images. Based on the time phase adjustment between the first and second sequential images, the thumbnails 410 to 490 may be displayed above the thumbnails 210 to 270 in the monitor 32. The thumbnails 210 to 270 are placed in display below the respective corresponding thumbnails 410 to 490 in accordance with the time phase adjustment. Therefore, for example, the thumbnail 260 may be placed and displayed below the thumbnail 470 while the thumbnails 210 to 250 may correspond to the thumbnails 410 to 450. Similarly, the thumbnail 270 may be placed and displayed below the thumbnail 490. There may be no thumbnails of the two-chamber view images which correspond to the thumbnails 460 and 480 according to the time phase adjustment.

As shown in FIG. 13, when the operator points by a cursor and selects, for example, the thumbnail 470 of the four-chamber view image, an enlarged image (OG470 in FIG. 14) corresponding to the selected thumbnail 470 may be displayed. The enlarged image may be an original image, included in the first sequential images, corresponding to the thumbnail 470. FIG. 14 is an illustration showing an example of a parallel display after the thumbnails display according to the second embodiment of the present invention. When the enlarged image OG470 corresponding to the selected thumbnail 470 is displayed, another enlarged image OG260 corresponding to the thumbnail 260 may also be displayed in the monitor 32. The another enlarged image OG260 may be an original image, included in the second sequential images, corresponding to the thumbnail 260. Responsive to the selection of the thumbnail 470, the enlarged image OG470 and the another enlarged image OG260 may be displayed in parallel as shown in FIG. 14. Also when the operator selects the thumbnail 260, both the enlarged images OG470 and OG260 may be similarly displayed responsive to the selection. If, however, the operator selects the thumbnail 460, only an enlarged image corresponding to the thumbnail 460 may be displayed since there is no thumbnail of the two-chamber view image, which corresponds to the thumbnail 460. In other words, there is no two-chamber view image corresponding, in time phase, to a four-chamber view image which is a base of the thumbnail 460.

The first and second embodiments of the present invention may not be limited to a time phase adjustment between two kinds of sequential image data, but may also be applied to a time phase adjustment among more than two kinds of sequential image data. In the case of more than two kinds of sequential image data, one of the more than two kinds of sequential image data may be selected as base sequential image data, as similar to the case of two kinds of sequential image data. Once one base sequential image data is selected and determined, each of all the other sequential image data is rendered to be adjusted its time phase with a time phase of the determined one base sequential image data as explained in the first embodiment of the present invention. After such a time phase adjustment among the more than two kinds of sequential image data, images included in the more than two kinds of sequential image data are displayed every kind in parallel. Alternatively, the operator may select one or more specific kinds of sequential image data in advance or at the time of display. If the operator selects only one kind of sequential image data, only the selected one sequential image data are displayed in the monitor 32, regardless of the time phase adjustment. On the other hand, if the operator selects any two or more specific kinds of sequential image data, such selected two or more kinds of sequential image data are displayed in parallel in the monitor 32 in accordance with the time phase adjustment. Such selection may be advantageous if the operator prefers to concentrate on specific kinds of sequential image data in comparison, not all kinds of sequential image data.

FIG. 15 is an illustration showing another example of thumbnails, displayed in parallel, of the time-phase adjusted three kinds of sequential images according to the second embodiment of the present invention. In FIG. 15, thumbnails 410 to 490 correspond to sequential image data of a first cross-sectional view (hereinafter referred to as first cross sectional view image data) and are a base of a time phase adjustment for both thumbnails 210 to 270 corresponding to sequential image data of a second cross-sectional view (hereinafter referred to as second cross sectional view image data) and thumbnails 310 to 370 corresponding to sequential image data of a third cross-sectional view (hereinafter referred to as third cross sectional view image data). In accordance with the time phase adjustment among the first, second, and third cross sectional view image data on the basis of the first cross sectional view image data, the thumbnails 410 to 490 may be displayed above the thumbnails 210 to 270 in the monitor 32. Further, the thumbnails 310 to 370 may be displayed below the thumbnails 210 to 270 in the monitor 32. The thumbnails 210 to 270 are placed in display below the respective corresponding thumbnails 410 to 490 in accordance with the time phase adjustment. Further, the thumbnails 310 to 370 are placed in display in a manner corresponding to thumbnails 410 to 490 in accordance with the time phase adjustment. Therefore, for example, the thumbnail 260 may be placed and displayed below the thumbnail 470 while the thumbnails 210 to 250 may correspond to the thumbnails 410 to 450. Further, the thumbnail 270 may be placed and displayed below the thumbnail 490. There may be no thumbnails of the second cross sectional view image data which correspond to the thumbnails 460 and 480 according to the time phase adjustment. Similarly, for example, the thumbnail 350 may be placed and displayed below the thumbnail 460 while the thumbnails 310 to 340 may correspond to the thumbnails 410 to 440. Further, the thumbnails 360 and 370 may be placed and displayed below the thumbnails 480 and 490. There may be no thumbnails of the third cross sectional view image data which correspond to the thumbnails 450 and 470 according to the time phase adjustment. When there are obtained three or more kinds of sequential image data, such as, for example, the first, second, and third cross sectional view image data, the operator may select any two or more of the three or more kinds of sequential image data. In other words, in the case shown in FIG. 15, for example, the thumbnails 410 to 490 and 310 to 370 may be displayed together while the thumbnails 210 to 270 may not be displayed. Alternatively, for example, the thumbnails 210 to 270 and 310 to 370 may be displayed together while the thumbnails 410 to 490 may not be displayed. Such a selection may not only be applied to the display of thumbnails, but also be applicable to the display of original image data (two or more kinds of sequential image data) in a sequential display manner.

As described above, according to the second embodiment of the present invention, a plurality of sequential image data acquired under respective different conditions are adjusted in their relative time phases. Further, the plurality of sequential image data may be displayed simultaneously. Therefore, it may be possible to observe motor functions of the heart in a three dimensional manner more accurately. In addition, it may also be possible to easily see an influence by, for example, an exercise stress.

Embodiments according to the present invention have been described on an example of sequential image data representing the four-chamber view and the two-chamber view. Embodiments according to the present invention may not be limitedly applied to the above example, but may also be applied to sequential image data representing a major axis view and a minor axis view, to sequential image data representing a view before the exercise stress and a view after the exercise stress, and the like. The stress may alternatively be caused pharmacologically. When images corresponding to those image data are displayed in the monitor 32, the images may not be limited to B-mode images, but may also be Doppler-mode images which reflect a status of tissue exercises or blood streams. The images may alternatively be images synthesizing the B-mode images and the Doppler-mode images. According to embodiments of the present invention, it may be preferable to display the sequential images as a moving image, but may be possible to display the sequential images as static images as long as, when at least two kinds of sequential images are displayed in parallel, such static images of the respective sequential images are displayed one after the other in the time-phase adjusted manner.

Figure 16:
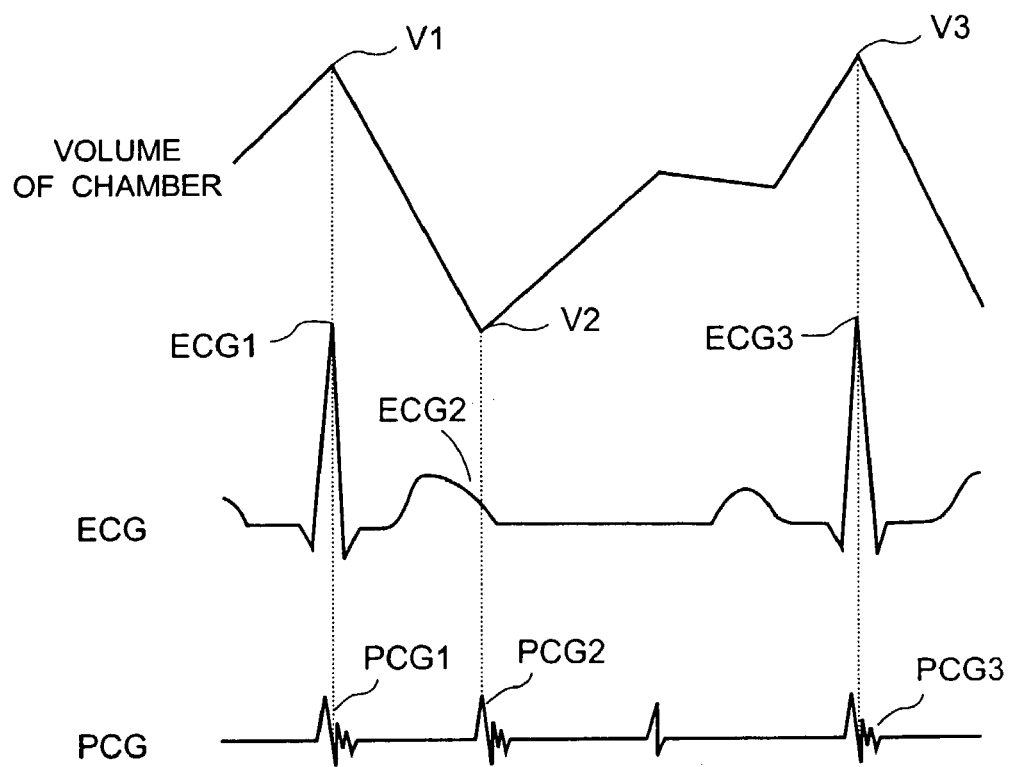
FIG. 16 is a chart showing an example of a relationship among volume data of the heart chamber, electrocardiogram data, and phonocardiogram data according to embodiments of the present invention.

In the above embodiments of the present invention, the end-diastolic time and the end-systolic time have been determined based on the calculated volume or the like of the heart chamber. However, the end-diastolic time and the end-systolic time may be determined by another way. FIG. 16 is a chart showing an example of a relationship among volume data of the heart chamber, electrocardiogram data, and phonocardiogram data according to embodiments of the present invention.

In FIG. 16, a first end-diastolic time V1 according to the volume data of the heart chamber may correspond to a first R wave ECG1 of the electrocardiogram data as described before. On the other hand, a first heart sound (or a first wave form in the phonocardiogram) PCG1 of the phonocardiogram data may not be clear enough to determine the first end-diastolic time V1. Therefore, a time of the first R wave ECG1 may be assumed to be a first end-diastolic time corresponding to the first end-diastolic time V1. When it comes to an end-systolic time, an end-systolic time V2 according to the volume data of the heart chamber may correspond to a second heart sound PCG2 (or a second wave form in the phonocardiogram) of the phonocardiogram data. This time, a wave ECG2 of the electrocardiogram data may not be clear enough to specify the end-systolic time V2. Therefore, a time of the second heart sound PCG2 may be assumed to be an end-systolic time corresponding to the end-systolic time V2. Similar to the first end-diastolic time, a second end-diastolic time V3 according to the volume data of the heart chamber may correspond to a second R wave ECG3 of the electrocardiogram data as described before. On the other hand, another first heart sound PCG3 of the phonocardiogram data may not be clear enough to determine the second end-diastolic time V3. Therefore, a time of the second R wave ECG3 may be assumed to be a second end-diastolic time corresponding to the second end-diastolic time V3. Therefore, it may be possible to determine the first and second end-diastolic times and the end-systolic time without calculating a volume or the like of the respective sequential image data, regarding respective kind of sequential image data.

The ultrasound diagnosis apparatus has been described according to embodiments of the present invention. The feature of time-phase adjustment may not be essentially incorporated in the ultrasound diagnosis apparatus. According to alternative embodiments of the present invention, the feature may be provided in a data processor, which is independent from an ultrasound diagnosis apparatus. The data processor may be placed in a location different (or remote) from the ultrasound diagnosis apparatus and be connected to and provided ultrasound images from the ultrasound diagnosis apparatus. Further, those skilled in the art will appreciate that a data processor, according to such an embodiment, may be implemented as one or more processing devices. Accordingly, even if the ultrasound diagnosis apparatus is a conventional apparatus, it may be possible to enjoy the feature of the time-phase adjustment according to such alternative embodiments of the present invention.

Figure 17:
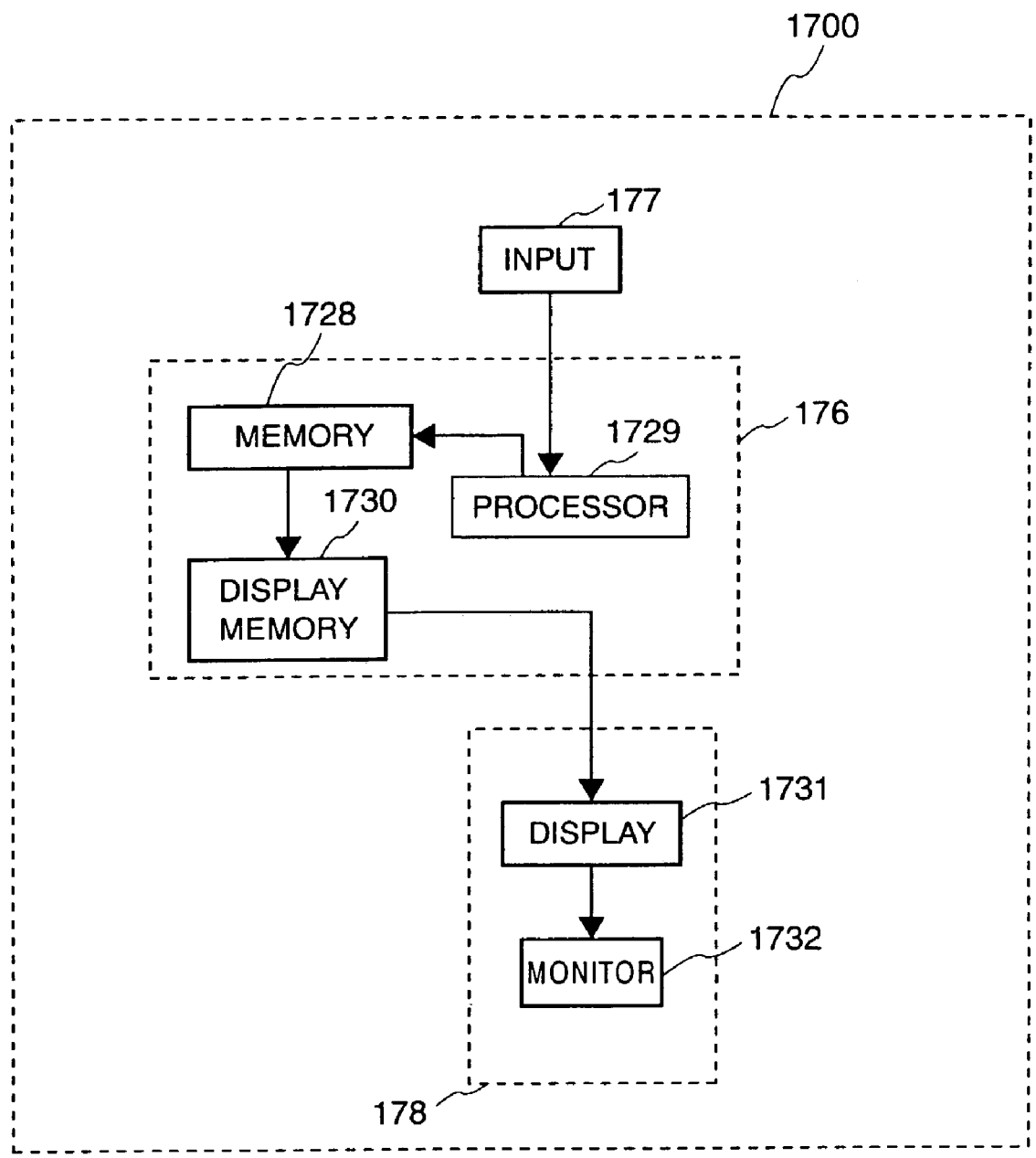
FIG. 17 is a block diagram showing an exemplary configuration of a data processor according to embodiments of the present invention.

FIG. 17 is a block diagram showing an exemplary configuration of a data processor according to embodiments of the present invention. A data processor 1700 may include an image measurement unit 176, an input unit 177, and a display unit 178.

The image measurement unit 176 may include a memory 1728, a processor 1729, and a display memory 1730. The display unit 178 may include a display circuit 1731 and a monitor 1732. Image data to be processed in the data processor 1700 may be obtained through a detachable storage media storing the image data acquired from an ultrasound diagnosis apparatus or through a communication cable connected to an ultrasound diagnosis apparatus. Details of each component included in the data processor 1700 and procedures thereby may be similar to those described in the first embodiment of the present invention. Therefore, further description of the components and related procedures are omitted herein. As long as sequential image data are supplied to the data processor 1700, any type of conventional ultrasound diagnosis apparatus can benefit the feature of the time phase adjustment according to embodiments of the present invention.

Several embodiments of the present invention have been described above. However, embodiments of the present invention may not be limited to those embodiments, but may be modified within a scope of the present invention. For example, embodiments of the present invention may be applicable to images acquired from an X-ray diagnosis apparatus, an X-ray computed tomography apparatus, a magnetic resonance imaging apparatus, or the like as well as the ultrasound diagnosis apparatus. Further, the embodiments of the present invention described above have primarily shown the time phase adjustment between the two kinds of sequential image data on the basis of the time-series volume transition of the internal space of the heart chamber. The time phase adjustment according to embodiments of the present invention may also be obtained on the basis of a time-series area transition of the internal space of the heart chamber extracted by a predetermined automated contour extraction technique. Further, the time phase adjustment according to embodiments of the present invention may be obtained on the basis of a time-series length transition of the internal space of the heart chamber along the long axis. Still further, the embodiments of the present invention described above have been described on the measurement of a ventricle (e.g., a left ventricle). Embodiments of the present invention may alternatively be applied to a measurement of an atrial.

Still further, according to the embodiments of the present invention described above, the ultrasound diagnosis apparatus has acquired and sequentially stored a predetermined number of sequential image data in the memory 28 in accordance with the command signals indicating an initiation of the image data acquisition in the four-chamber view and two-chamber view image data acquisition. The command signals have been input from the input unit 7. Alternative image data acquisition techniques, however, may be applied to embodiments of the present invention. For example, in the four-chamber view and two-chamber view image data acquisitions, the operator may operate the input unit 7 to input command signals indicating an image data acquisition while images are being displayed in the monitor 32 through the memory 28 in real time. Responsive to the command signals, the memory 28 may be operative to store a predetermined number of sequential image data before the input timing of the command signals. In other words, a predetermined number of sequential image data may be stored in the memory 28 retroactive to a past image which has been acquired the predetermined number of images before the input timing of the command signals.

In the above embodiments of the present invention, the sequential image data representing the four-chamber view may have been acquired prior to the sequential image data representing the two-chamber view. However, as long as it is not restricted, the order of acquiring two kinds of sequential image data may not be limited to that described in the above embodiments of the present invention.

Still furthermore, in the embodiments of the present invention, the ultrasound diagnosis apparatus or the data processor may have a random access memory (RAM), which can receive and store computer programs and applications as computer readable instructions in a temporary and/or non-volatile state. The ultrasound diagnosis apparatus or the data processor may further have a hard disk drive as part of the controller for reading from and writing to a hard disk, a magnetic disk drive for reading from and writing to a magnetic disk, and/or an optical disk drive for reading from and writing to an optical disk (such as a CD, CDR, CD-RW, DVD, or other optical device). Those skilled in the art will appreciate that one or more of such memory, drives, and their respective media are examples of a computer program product for storing computer readable instructions, which when executed, may implement an embodiment of the present invention.

Accordingly, an apparatus, which does not incorporate features of embodiments of the present invention can benefit the features as long as the apparatus is equipped with a feature of reading and performing a computer readable program.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

What is claimed is:

1. An ultrasound diagnosis apparatus, comprising
an insonifier configured to insonify an ultrasound to a specimen;
a receiver configured to receive an echo signal from the specimen resulting from the ultrasound; and
a processor in communication with the receiver, the processor being configured to process the echo signal so as to obtain a first series of images under a first condition and a second series of images under a second condition,
the processor further being configured to measure a first physical value on the first series of images and a second physical value on the second series of images, and
the processor further being configured to adjust a time phase of the second series of images relative to a time phase of the first series of images based on the first physical value and the second physical value,
wherein the processor is further configured to determine a number (N1) of images in the first series of images that are included in a first predetermined period, determine a number (N2) of images in the second series of images that are included in a second predetermined period,
wherein a first image interval time (T1) is a time between each of the first series of images, and a second image interval time (T2) is a time between each of the second series of images, said interval time T1 and said interval time T2 are based on the first physical value and the second physical value, respectively, and
wherein the processor is further configured to calculate a coefficient (C) represented in a formula: C=(N2×T2)/(N1×T1), and adjust the time phase of the second series of images relative to the first series of images based on the coefficient C.

2. The apparatus according to claim 1, further comprising a display configured to display the first physical value and the second physical value in a chart form.

3. The apparatus according to claim 2, wherein the first physical value and the second physical value are displayed in time phase in accordance with the time phase adjustment.

4. The apparatus according to claim 1, wherein the processor is further configured to calculate a third physical value based on the first physical value and the second physical value in accordance with the time phase adjustment.

5. The apparatus according to claim 4, further comprising a display coupled to the processor and configured to display the third physical value in a chart form.

6. The apparatus according to claim 1, further comprising a display coupled to the processor and configured to display the first series of images and the second series of images in accordance with the time phase adjustment.

7. The apparatus according to claim 6, wherein the first series of images and the second series of images are displayed in time phase in a manner of a moving image.

8. The apparatus according to claim 6, wherein the first series of images and the second series of images are sequentially displayed in time phase in a manner of a still image.

9. The apparatus according to claim 1, further comprising a display configured to display first thumbnails of the first series of images and second thumbnails of the second series of images in accordance with the time phase adjustment.

10. The apparatus according to claim 9, further comprising an input device coupled to the processor and configured to select one or more of the first thumbnails; and wherein the display is further configured to display one or more of the first series of images, corresponding to the selected one or more of the first thumbnails, and wherein the display is further configured to display one or more of the second series of images, corresponding to the one or more of the first series of images in a time phase adjusted manner.

11. The apparatus according to claim 1, wherein each of the first physical value and the second physical value represents a volume of a predetermined part of the specimen.

12. The apparatus according to claim 1, wherein each of the first physical value and the second physical value represents an area of a predetermined part of the specimen.

13. The apparatus according to claim 1, wherein each of the first physical value and the second physical value represents a length of a predetermined part of the specimen.

14. The apparatus according to claim 1, wherein the first condition is an echocardiography for obtaining the first series of images of a four-chamber view of a heart of the specimen, and wherein the second condition is an echocardiography for obtaining the second series of images of a two-chamber view of the heart.

15. The apparatus according to claim 1, wherein the first condition is an echocardiography for obtaining the first series of images of a heart of the specimen along a major axis of the heart, and wherein the second condition is an echocardiography for obtaining the second series of images of the heart along a minor axis of the heart.

16. The apparatus according to claim 1, wherein the first condition is an echocardiography for obtaining the first series of images before a pharmacologic stress to the specimen, and wherein the second condition is an echocardiography for obtaining the second series of images after the pharmacologic stress to the specimen.

17. The apparatus according to claim 1, wherein the first condition is an echocardiography for obtaining the first series of images before an exercise stress to the specimen, and wherein the second condition is an echocardiography for obtaining the second series of images after the exercise stress to the specimen.

18. The apparatus according to claim 1, wherein, when the first series of images and the second series of images are obtained under an echocardiography, the processor adjusts a time phase of a systolic period of the second series of images relative to a time phase of a systolic period of the first series of images.

19. The apparatus according to claim 1, wherein, when the first series of images and the second series of images are obtained under an echocardiography, the processor adjusts a time phase of a diastolic period of the second series of images relative to a time phase of a diastolic period of the first series of images.

20. The apparatus according to claim 1, wherein, when the first series of images and the second series of images are obtained under an echocardiography, the processor adjusts an end-systolic time of the second series of images relative to an end-systolic time of the first series of images.

21. The apparatus according to claim 1, wherein, when the first series of images and the second series of images are obtained under an echocardiography, the processor adjusts an end-diastolic time of the second series of images relative to an end-diastolic time of the first series of images.

22. The apparatus according to claim 1, wherein, when the first series of images and the second series of images are obtained under an echocardiography, the first predetermined period represents a systolic period of the first series of images and the second predetermined period represents a systolic period of the second series of images.

23. The apparatus according to claim 1, wherein, when the first series of images and the second series of images are obtained under an echocardiography, the first predetermined period represents a diastolic period of the first series of images and the second predetermined period represents a diastolic period of the second series of images.

24. An ultrasound diagnosis apparatus, comprising:
an insonifier configured to insonify an ultrasound to a specimen;
a receiver configured to receive an echo signal from the specimen resulting from the ultrasound;
a processor in communication with the receiver, the processor being configured to process the echo signal so as to obtain a first series of images when insonified under a first condition and a second series of images when insonified under a second condition;
a first interface configured to receive electrocardiogram data; and
a second interface configured to receive phonocardiogram data,
wherein the processor detects the first, the third, the fourth, and the sixth characteristic times based on the electrocardiogram data and the second and the fifth characteristic times based on the phonocardiogram data,
the processor further being configured to detect a first, a second, and a third characteristic times in a first predetermined period when the first series of images have been obtained and a fourth, a fifth, and a sixth characteristic times in a second predetermined period when the second series of images have been obtained, and
the processor further being configured to adjust a time phase of the first series of images and a time phase of the second series of images based on the first to the sixth characteristic times.

25. The apparatus according to claim 24 wherein each of the first, the third, the fourth, and the sixth characteristic times is relative to an R-wave included in the electrocardiogram data, and wherein each of the second and the fifth characteristic times is relative to a second heart sound included in the phonocardiogram data after the occurrence of the R-wave.

26. A medical image apparatus, comprising:
a generator configured to generate a first series of medical images of a specimen under a first condition and a second series of medical images of the specimen under a second condition; and a processor in communication with the generator, the processor being configured to measure a first physical value on the first series of medical images and a second physical value on the second series of medical images, and to adjust a time phase of the second series of medical images relative to a time phase of the first series of medical images based on the first physical value and the second physical value,
wherein the first physical value and the second physical value represent at least one of a volume of a portion of the specimen, an area of the specimen, and a length of a predetermined part of the specimen.

27. A computer program product on which is stored a computer program for adjusting a time phase of a second series of medical data obtained under a second condition in a medical equipment relative to a time phase of a first series of medical data obtained under a first condition in the medical equipment, the computer program having instructions, which when executed, perform steps comprising:
measuring a first physical value on the first series of medical data;
measuring a second physical value on the second series of medical data; and
adjusting the time phase of the second series of medical data relative to the time phase of the first series of medical data based on the first physical value and the second physical value,
wherein the first physical value and the second physical value represent at least one of a volume of a portion of the specimen, an area of the specimen, and a length of a predetermined part of the specimen.

28. A medical image apparatus, comprising:
a generator configured to generate a first series of medical images representative of a specimen during a first period and a second series of medical images representative of a specimen during a second period different from the first period; and
a processor in communication with the generator, the processor being configured to measure a first physical value on the first series of medical images and a second physical value on the second series of medical images and to adjust a time phase of the second series of medical images relative to a time phase of the first series of medical images based on the first physical value and the second physical value,
wherein the first physical value and the second physical value represent at least one of a volume of a portion of the specimen, an area of the specimen, and a length of a predetermined part of the specimen.

29. A medical diagnostic apparatus that adjusts a time phase between a plurality of image series, comprising:
a transmitter configured to provide a first signal to a specimen;
a receiver configured to receive a second signal from the specimen that is related to the first signal;
a processor in communication with the receiver that receives the second signal from the receiver; and
a memory storage device coupled to the processor, the memory storage device storing the image series;
wherein the processor is operative to:
generate a plurality of data sets from the second signal and store each of the data sets as the image series within the memory storage device;
determine a profile from each of the image series; and
adjust the profile of a first of the image series relative to the profile of a second of the image series based upon a comparison of a physical value determined from each of the first of the image series and the second of the image series, wherein the first physical value represents at least one of a volume of a portion of the specimen, an area of the specimen, and a length of a predetermined part of the specimen.

30. The medical diagnostic apparatus according to claim 29, further comprising a display coupled to the processor for displaying the adjusted profile of the first of the image series relative to the profile of the second of the image series.

31. The medical diagnostic apparatus according to claim 29, wherein the processor is further operative to adjust the profile of a third of the image series relative to the profile of the second of the image series based upon a comparison of a physical value determined from each of the second of the image series and the third of the image series.

32. An ultrasound diagnosis apparatus, comprising:
a radiation unit configured to radiate an ultrasound to an object;
a receiving unit configured to receive an echo signal from the object resulting from the ultrasound radiation; and
a processor in communication with the receiver, the processor including:
an acquisition unit configured to process so as to acquire a first series of images under a first condition and a second series of images under a second condition, respectively;
a measuring unit configured to measure a first physical value for the first series of images and a second physical value for the second series of images, respectively; and
an adjusting unit configured to adjust a time phase of an ending contraction period or an expansion period of the first series of images and the second series of images based on the first physical value and the second physical value,
wherein the first physical value and the second physical value represent at least one of a volume, an area or a length of a predetermined part of the heart.

* * * * *